United States Patent
McFadden

(10) Patent No.: US 10,945,980 B2
(45) Date of Patent: Mar. 16, 2021

(54) TREATMENT FOR MYOPIA

(71) Applicant: The University of Newcastle, Callaghan (AU)

(72) Inventor: Sally Anne McFadden, Cooks Hill (AU)

(73) Assignee: The University of Newcastle, Callaghan (AU)

(*) Notice: Subject to any disclaimer, the term of this patent is extended or adjusted under 35 U.S.C. 154(b) by 0 days.

(21) Appl. No.: 16/310,587

(22) PCT Filed: Jun. 21, 2017

(86) PCT No.: PCT/AU2017/050627
§ 371 (c)(1),
(2) Date: Dec. 17, 2018

(87) PCT Pub. No.: WO2017/219080
PCT Pub. Date: Dec. 28, 2017

(65) Prior Publication Data
US 2019/0142778 A1 May 16, 2019

(30) Foreign Application Priority Data
Jun. 21, 2016 (AU) ................................ 2016902429

(51) Int. Cl.
*A61K 31/19* (2006.01)
*A61P 27/02* (2006.01)
*A61K 31/198* (2006.01)
*A61P 27/10* (2006.01)
*A61K 9/00* (2006.01)

(52) U.S. Cl.
CPC .......... *A61K 31/198* (2013.01); *A61K 9/0048* (2013.01); *A61P 27/02* (2018.01); *A61P 27/10* (2018.01)

(58) Field of Classification Search
CPC ................................ A61K 31/19; A61P 27/02
USPC ........................................................ 514/565
See application file for complete search history.

(56) References Cited

FOREIGN PATENT DOCUMENTS

| WO | WO 00/54773 A1 | 9/2000 |
| WO | WO 01/10406 A2 | 2/2001 |
| WO | WO 02/24191 A1 | 3/2002 |

OTHER PUBLICATIONS

Beauregard, Clay et al., "Effects of Nitric Oxide Donors and Nitric Oxide Synthase Substrates on Ciliary Muscle Contracted by Carbachol and Endothelin for Possible Use in Myopia Prevention" Journal of Ocular Pharmacology and Therapeutics, 2001, pp. 1-9, vol. 17, No. 1.
Huibi, Xu et al., "Prevention of Axial Elongation in Myopia by the Trace Element Zinc" Biological Trace Element Research, 2001, pp. 39-40, vol. 79.
Maggesissi, R.S. et al., "Modulation of GABA release by nitric oxide in the chick retina: Different effects of nitric oxide depending on the cell population" Vision Research, 2009, pp. 2494-2502, vol. 49.
International Search Report for PCT/AU2017/050627 dated Oct. 4, 2017.
McBrien, Neville A. et al., "Point-counterpoint—How does atropine exert its anti-myopia effects?" Ophthalmic Physiol Opt, 2013, pp. 373-378, vol. 33.
Mutti, Donald O. et al., "Accommodative Lag before and after the Onset of Myopia" Invest Ophthalmol Vis Sci., 2006, pp. 837-846, vol. 47.
Troilo, David et al., "IMI—Report on Experimental Models of Emmetropization and Myopia" Invest Ophthalmol Vis Sci., 2019, pp. M31-M88, vol. 60, No. 3.

*Primary Examiner* — Raymond J Henley, III
(74) *Attorney, Agent, or Firm* — Knobbe Martens Olson & Bear LLP

(57) ABSTRACT

Provided herein are methods for treating or preventing myopia, or for inhibiting the development of myopia, comprising administering to a subject in need thereof an effective amount of an agent capable of increasing nitric oxide levels in one or more ocular cells or an agent capable of promoting or increasing the expression and/or activity of nNOS in one or more ocular cells. Also provided are methods for inducing or promoting nNOS expression and/or activity in one or more ocular cells, comprising exposing said cells to an effective amount of L-arginine.

8 Claims, 10 Drawing Sheets

A

B

TREATMENT FOR MYOPIA

CROSS REFERENCE TO RELATED APPLICATIONS

This application is a U.S. National Phase Application of PCT International Application Number PCT/AU2017/050627, filed on Jun. 21, 2017, designating the United States of America and published in the English language, which is an International Application of and claims the benefit of priority to Australian Patent Application No. 2016902429, filed on Jun. 21, 2016. The disclosures of the above-referenced applications are hereby expressly incorporated by reference in their entireties.

TECHNICAL FIELD

The present disclosure relates generally to methods and compositions for treating myopia.

BACKGROUND OF THE DISCLOSURE

Myopia or "short-sightedness" affects more than 2 billion people worldwide, with prevalence on the rise around the world, most dramatically in Asia. Although pathological forms of myopia can occur at birth, myopia is generally a progressive disease, with up to 15% of myopes developing high myopia. High myopia is associated with cataract, glaucoma, retinal detachment, myopic macular degeneration and irreversible visual loss. The high prevalence rates of myopia are strongly associated with increased urbanization and education implicating environmental causes. Furthermore, myopia can be acquired through aberrant visual input. For example, deprivation of detailed vision (form deprivation) can cause myopia, while myopia can also develop if vision is degraded through cataracts or if the eye experiences hyperopic defocus, such as can occur during reading or when young eyes wear negative spectacle or contact lenses.

Myopia occurs when light entering the eye focuses in front of the retina instead of directly on it. This is caused by an increase in optical power, such as a cornea that is steeper and/or an eye that is longer than a normal eye. Myopia often manifests in children, becoming progressively worse through adolescence. Symptoms may include blurry distance vision and/or vision that seems clearer upon squinting. In progressive and degenerative myopia, there is progressive elongation of the eye and thinning of the sclera. The elongation is accompanied by a thinner retina and choroid. The increase in eye size is greatest at the posterior pole of the eye which encompasses the optic nerve and is near the sensitive macular region, and can lead to the formation of a focal bulges, or staphyloma, in the weakened sclera. As the tissues distort, the underlying retina is compromised and retinal cells atrophy, causing irreversible visual loss. There is currently no proven effective, viable treatment for progressive myopia, either in terms of preventing the progression of myopia, or reversing myopia. Specialised spectacles and contact lenses can provide partial treatment, while natural light stimulation and wavelength manipulation have also been proposed. Atropine is used off-label to prevent myopia-progression. However high doses of atropine (0.5% to 1%) are required to maximise efficacy and these are associated with unacceptable side effects such as blurred vision and photophobia. Discontinuance is also associated with a rebound effect.

There is a clear need for the development of novel, effective therapies to treat myopia, inhibit or prevent the progression of myopia and to prevent the development of myopia.

Nitric oxide (NO) acts as a neural modulator in the retina, and is expressed in all vertebrate eyes. It is biosynthesised endogenously from arginine and oxygen, the reaction catalyzed by one of three isoforms of nitric oxide synthase (NOS): neuronal NOS (nNOS or bNOS), endothelial NOS (eNOS) and inducible or macrophage NOS (iNOS), classified according to the cell types from which they derive. The nNOS isoform is the most commonly expressed in the retina.

Based on the findings described and exemplified herein, wherein the inventors have demonstrated that nNOS expression is down regulated in myopic eyes, the inventors provide novel means of treating myopia, inhibiting or preventing the progression of myopia and preventing the development of myopia.

SUMMARY OF THE DISCLOSURE

A first aspect of the present disclosure provides a method for treating or preventing myopia, or for inhibiting the development of myopia, the method comprising administering to a subject in need thereof an effective amount of an agent capable of increasing nitric oxide levels in one or more ocular cells.

In particular embodiments the agent is a nitric oxide synthase substrate or a nitric oxide donor.

In a particular embodiment, the agent induces or promotes the expression and/or activity of neuronal nitric oxide synthase (nNOS), endothelial nitric oxide synthase (eNOS) or inducible nitric oxide synthase (iNOS) in the one or more ocular cells, thereby leading to increased production of nitric oxide. Accordingly, the NOS substrate may be a substrate of nNOS, eNOS or iNOS, more particularly of nNOS.

In exemplary embodiments the agent is a NOS substrate, in particular L-arginine. In exemplary embodiments the NOS is nNOS.

Typically the ocular cells express nNOS or are part of an nNOS producing structure in the eye. In an exemplary embodiment the cells are amacrine cells. An exemplary agent that induces or promotes the expression and/or activity of nNOS in amacrine cells is L-arginine.

In particular embodiments the agent is administered directly to an eye of the subject. The agent may be administered to amacrine cells of the retina or other nitric oxide producing cells of the eye.

The agent may be administered, for example, orally or topically, such as in eye drops, an eye wash solution, an ointment or gel. Administration may be, for example, once per day or twice per day. In an alternative embodiment the agent may be conjugated to, or coated on, the surface of a contact lens or the contact lens may be impregnated with the agent. Alternatively the agent may be administered by injection directly into a specific tissue or region of the eye, such as into the conjunctiva or sclera. Thus, the agent may be administered by, for example, intravitreal, conjunctival or scleral injection, or an intraocular implant or other slow release delivery method.

The myopia may be, for example, lens- or instrument-induced myopia, simple myopia, early or late-onset myopia, progressive myopia, degenerative myopia or pathological myopia. The treatment, prevention or inhibition of development of myopia may comprise inhibiting or preventing the progression of myopia in a myopic eye. Alternatively, the treatment, prevention or inhibition of development of myopia may comprise reversing established myopia. Alternatively, the treatment, prevention or inhibition of development of myopia may comprise inhibiting or preventing the development of myopia in an eye predisposed thereto or at risk of developing myopia.

A second aspect of the present disclosure provides a method for treating or preventing myopia or for inhibiting the development of myopia, the method comprising administering to a subject in need thereof an effective amount of an agent capable of promoting or increasing the expression and/or activity of nNOS in one or more ocular cells.

Typically the ocular cells express nNOS or are part of an nNOS producing structure in the eye. In an exemplary embodiment the cells are amacrine cells.

In particular embodiments the agent is administered directly to an eye of the subject. The agent may be administered to amacrine cells of the retina or other nitric oxide producing cells of the eye.

The agent may be administered, for example, orally or topically, such as in eye drops, an eye wash solution, an ointment or gel. Administration may be, for example, once per day or twice per day. In an alternative embodiment the agent may be conjugated to, or coated on, the surface of a contact lens or the contact lens may be impregnated with the agent. Alternatively the agent may be administered by injection directly into a specific tissue or region of the eye, such as into the conjunctiva or sclera. Thus, the agent may be administered by, for example, intravitreal, conjunctival or scleral injection, or an intraocular implant or other slow release delivery method.

In a particular embodiment the agent is L-arginine.

The myopia may be, for example, lens- or instrument-induced myopia, simple myopia, early or late-onset myopia, progressive myopia, degenerative myopia or pathological myopia. The treatment, prevention or inhibition of development of myopia may comprise inhibiting or preventing the progression of myopia in a myopic eye. Alternatively, the treatment, prevention or inhibition of development of myopia may comprise reversing established myopia. Alternatively, the treatment, prevention or inhibition of development of myopia may comprise inhibiting or preventing the development of myopia in an eye predisposed thereto or at risk of developing myopia.

A third aspect of the present disclosure provides a method for inducing or promoting nNOS expression and/or activity in one or more ocular cells to thereby increase the production of nitric oxide, the method comprising exposing said cells to an effective amount of L-arginine.

Typically the ocular cells express nNOS or are part of an nNOS producing structure in the eye. In an exemplary embodiment the cells are amacrine cells.

A fourth aspect of the present disclosure provides the use of a nitric oxide synthase substrate or nitric oxide donor in the manufacture of a medicament for treating or preventing myopia or for inhibiting the development of myopia.

A fifth aspect of the present disclosure provides the use of an agent capable of promoting or increasing the expression and/or activity of nNOS in one or more ocular cells in the manufacture of a medicament for treating or preventing myopia or for inhibiting the development of myopia.

BRIEF DESCRIPTION OF THE DRAWINGS

Embodiments of the present disclosure are described herein, by way of non-limiting example only, with reference to the following figures.

DETAILED DESCRIPTION

Figure 1:
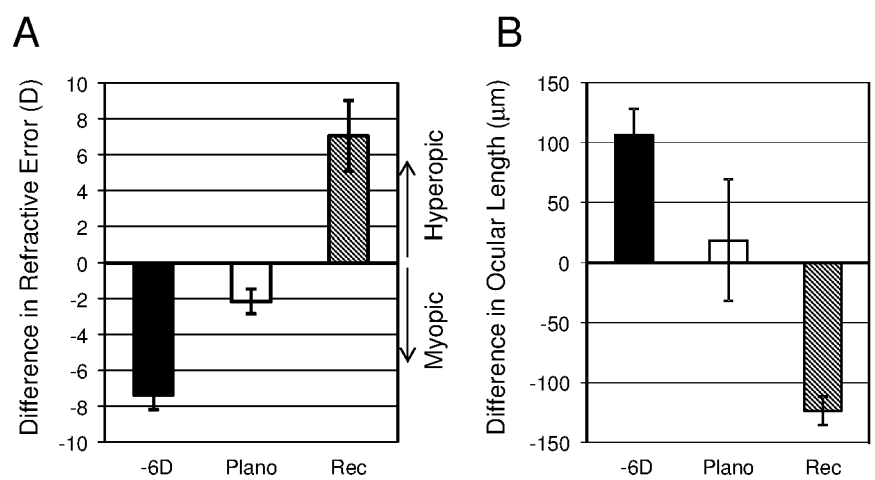
FIG. 1. A. Change in the difference in refractive error, and B. Change in the difference in ocular length, in three treatment groups of guinea pigs (Example 1). In animals wearing −6D or 0D (plano) lenses, the change is between the beginning and end of lens-wear. In recovery animals (Rec), the change is before and after recovery. The data shows that the guinea pig eye is sensitive to the sign of imposed defocus and changes its direction of ocular growth accordingly.

The articles "a" and "an" are used herein to refer to one or to more than one (i.e., to at least one) of the grammatical object of the article. By way of example, "an element" means one element or more than one element.

In the context of this specification, the term "about" is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

As used herein the terms "treating", "treatment", "preventing" and "prevention" refer to any and all uses which remedy myopia, prevent the establishment of myopia, or otherwise prevent, hinder, retard, or reverse the progression of myopia or one or more symptoms thereof. Thus the terms "treating" and "preventing" and the like are to be considered in their broadest context. For example, treatment does not necessarily imply that a patient is treated until total recovery. The treatment or prevention need not necessarily remedy, prevent, hinder, retard, or reverse all symptoms, of myopia but may prevent, hinder, retard, or reverse one or more symptoms. In some embodiments, methods of the present invention involve inhibiting or preventing the progression of myopia.

As used herein the term "effective amount" includes within its meaning a non-toxic but sufficient amount or dose of an agent or compound to provide the desired effect. The exact amount or dose required will vary from subject to subject depending on factors such as the species being treated, the age and general condition of the subject, the severity of myopia to be treated, the particular agent being administered and the mode of administration and so forth. Thus, it is not possible to specify an exact "effective amount". However, for any given case, an appropriate "effective amount" may be determined by one of ordinary skill in the art using only routine experimentation.

The term "subject" as used herein refers to mammals and includes humans, primates, livestock animals (e.g., sheep, pigs, cattle, horses, donkeys), laboratory test animals (e.g., mice, rabbits, rats, guinea pigs), companion animals (e.g., dogs, cats) and captive wild animals (e.g., foxes, kangaroos, deer). Typically, the subject is human or a laboratory test animal. Even more typically, the subject is a human.

As exemplified herein, the inventors have surprisingly found that myopia in guinea pigs reduces the number of displaced amacrine cells (DACs) expressing nNOS. The density of DACs expressing nNOS is sensitive to the sign of imposed defocus, such that the number of these cells expressing nNOS are decreased in myopic eyes that have increased growth and increased in eyes slowing their growth. Further, the inventors show that administration of L-arginine intravitreally increases the number of amacrine cells expressing nNOS. Further, the inventors show that administration of L-arginine to guinea pigs, either intravitreally, orally or by topical administration to the eye (e.g., eye drops), can prevent the development of myopia and inhibit the associated ocular elongation. Further, administration of an nNOS inhibitor is shown to inhibit recovery from myopia and promote ocular growth.

Accordingly, provided herein is a method for treating or preventing myopia or for inhibiting the development of myopia, the method comprising administering to a subject in need thereof an effective amount of an agent capable of increasing nitric oxide levels in one or more ocular cells. In exemplary embodiments, the agent is a nitric oxide synthase substrate or nitric oxide donor.

Also provided is a method for treating or preventing myopia or for inhibiting the development of myopia, the method comprising administering to a subject in need thereof an effective amount of an agent capable of promoting or increasing the expression and/or activity of nNOS in one or more ocular cells.

The treatment, prevention or inhibition of development of myopia may comprise inhibiting or preventing the progression of myopia in a myopic eye, reversing established myopia, or inhibiting or preventing the development of myopia in an eye predisposed thereto or at risk of developing myopia. The degree of myopia in an eye can be determined by those skilled in the art using routine analysis, including measurement of refractive error, ocular length determination, vitreous chamber depth and choroid thickness, in addition to clinical examination of the posterior retina and optic nerve. Such determinations may be used in diagnosing myopia to determine the suitability of a subject for treatment in accordance with the present invention, or may be used to monitor the progress of treatment and determine the efficacy of treatment using an agent as disclosed herein.

Myopia may be classified by a number of different criteria, including by cause, degree, age of onset, and clinical appearance. Those skilled in the art will appreciate that there are many different types or forms of myopia to which methods of the invention are applicable. For example, the myopia may be induced myopia, such as lens- or instrument-induced myopia, form deprivation myopia, index myopia, simple myopia, early or late-onset myopia, progressive myopia, degenerative myopia or pathological myopia or pseudomyopia. The myopia may be, for example, low, medium or high myopia. The myopia may be, for example, congenital myopia, childhood-onset myopia or adult-onset myopia.

As exemplified a particularly suitable agent for use in accordance with the present invention is a nitric oxide synthase substrate such as a substrate of nNOS, eNOS or iNOS. In exemplary embodiments the nitric oxide synthase substrate is L-arginine or an analogue thereof. L-arginine is a naturally occurring amino acid, which synthesises nitric oxide (NO) via nitric oxide synthase (NOS) and enhances the formation of NO. Oral L-arginine has been used safely in humans, rabbits, and rats and is commonly used to treat cardiovascular disease (Chin-Dusting et al, 2007). Those skilled in the art will appreciate that L-arginine is just one exemplary agent that may be employed in accordance with the present disclosure. Many other suitable agents are known to those skilled in the art and may be employed, for example NO donors such as organic nitrates (such as glyceryl trinitrate, isosorbide mononitrate and pentaerythrityl tetranitrate), sodium nitroprus side, diazeniumdiolates (NONOates), S-nitrothiols, and hybrid NO donor drugs (for reviews of NO donor drugs see, e.g.: Carpenter and Schoenfisch, 2012; Miller and Megson, 2007).

As exemplified herein, L-arginine induces or promotes the expression and/or activity of neuronal nitric oxide synthase (nNOS) in ocular cells. Typically the ocular cells express nNOS or are part of an nNOS producing structure in the eye. In an exemplary embodiment the cells are amacrine cells.

Accordingly, also disclosed herein is a method for inducing or promoting nNOS expression and/or activity in one or more ocular cells, the method comprising exposing said cells to an effective amount of L-arginine.

Agents such as L-arginine may be administered via any one of a number of suitable routes well known to those skilled in the art. Administration may be systemic or local. Suitable administration routes include, for example, parenteral, oral, and topical routes. For intraocular administration the agent may be delivered by injection (for example intravitreal, retinal, conjunctival, subconjunctival or scleral injection), or may be delivered topically (for example in eye drops, eye wash solution, ointment, gel, suspension, emulsion, or via a contact lens in which the agent is conjugated to the surface of, coated onto the surface of, or impregnated into, the contact lens) or via an intraocular implant or other slow release delivery means. Intraocular administration may comprise, for example, intravitreal, retinal, scleral, conjunctival or subconjunctival administration by any suitable means or in any suitable vehicle. Agents may be formulated with polymeric substances or in liposomes, nanoparticles or microspheres to facilitate delivery and/or to control release of the agent in the eye over a period of time. Those skilled in the art will appreciate that the scope of the present disclosure is not limited by any particular means or route of delivery of an active agent.

In an embodiment disclosed herein, the agent is administered by intravitreal injection to a subject in need thereof. In an embodiment disclosed herein, the agent is administered orally to a subject in need thereof. In an embodiment disclosed herein, the agent is administered by topical administration to a subject in need thereof (e.g., by eye drop).

An intraocular implant refers to a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye. In particular embodiments, intraocular implants are designed for intravitreal implantation. Implants may provide a sustained release of the agent, for example via a biodegradable polymer matrix. The formulation of suitable implants is within the capabilities and expertise of the skilled addressee.

Agents may also be administered in the form of liposomes. Liposomes may be derived from phospholipids or other lipid substances, and are formed by mono- or multi-lamellar hydrated liquid crystals dispersed in aqueous medium. Specific examples of liposomes used in administering or delivering a composition to target cells are DODMA, synthetic cholesterol, DSPC, PEG-cDMA, DLinDMA, or any other non-toxic, physiologically acceptable and metabolisable lipid capable of forming liposomes. The compositions in liposome form may contain stabilisers, preservatives and/or excipients. Methods for preparing liposomes are well known in the art, for example, see Methods in Cell Biology, Volume XIV, Academic Press, New York, N.Y. (1976), p. 33 ff., the contents of which are incorporated herein by reference.

It will be understood that the effective amount of an agent of the invention to be administered to any particular individual will depend upon a variety of factors including, for example, the activity of the specific agent employed, the age, body weight, general health and diet of the individual to be treated, the time of administration, the route of administration, rate of excretion, and combination with any other treatment or therapy. Single or multiple administrations can be carried out with amounts or dose levels and pattern being selected by the treating physician. A broad range of amounts and doses may be applicable. For example, considering administration to the retina, nanomolar or picomolar concentrations of the agent may be administered to a subject in need. Dosage regimens may be adjusted to provide the optimum therapeutic response. Those skilled in the art will appreciate that the more directly the agent is administered to, or close to, the retina, the lower the dose that will be required.

It will also be apparent to one of ordinary skill in the art that the optimal quantity and spacing of individual dosages will be determined by the nature and extent of the condition being treated, the form, route and site of administration, and the nature of the particular individual being treated. Also, such optimum conditions can be determined by conventional techniques known to those skilled in the art. For example, a subject may be administered the desired daily dose in a single unit dosage form once per day, or in two unit dosage forms administered twice a day. Divided doses may be administered daily, weekly, monthly or other suitable time intervals or the dose may be proportionally reduced as indicated by the exigencies of the situation.

It will also be apparent to one of ordinary skill in the art that the optimal course of treatment, such as, the number of doses of the composition given per day for a defined number of days, can be ascertained by those skilled in the art using conventional course of treatment determination tests.

In an embodiment disclosed herein, the nitric oxide synthase substrate is L-arginine and is administered to the subject in need thereof in an amount from about 25 mg/kg/day to about 1 g/kg/day, from about 50 mg/kg/day to about 500 mg/kg/day or from about 50 mg/kg/day to about 200 mg/kg/day. For example, the L-arginine may be administered in an amount of 25 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg or 1 g per kg per day. In an embodiment, the nitric oxide synthase substrate is L-arginine and is administered to the subject in need thereof in an amount from about 10 mg/kg/twice daily to about 500 mg/kg/twice daily, from about 20 mg/kg/twice daily to about 200 mg/kg/twice daily or from about 25 mg/kg/twice daily to about 100 mg/kg/twice daily.

In an embodiment disclosed herein, the nitric oxide synthase substrate is L-arginine and is administered by intravitreal, conjunctival or scleral injection to the subject in need thereof in an amount from about 0.01 mM to about 1 mM per day, from about 0.1 mM to about 0.5 mM per day, from about 0.15 mM to about 0.25 mM per day or in an amount of about 0.2 mM per day. For example, the L-arginine may be administered in an amount of about 0.01 mM, 0.05 mM, 0.1 mM, 0.15 mM, 0.2 mM, 0.25 mM, 0.3 mM, 0.35 mM, 0.4 mM, 0.45 mM, 0.5 mM, 0.55 mM, 0.6 mM, 0.65 mM, 0.7 mM, 0.75 mM, 0.8 mM, 0.85 mM, 0.9 mM, 0.95 mM or 1 mM per day.

In an embodiment disclosed herein, the nitric oxide synthase substrate is L-arginine and is administered by topical administration to the eye of the subject in need thereof in an amount from about 10 mM to about 500 mM per day, from about 50 mM to about 300 mM per day, from about 70 mM to about 200 mM per day or from about 100 mM to about 150 mM per day. For example, the L-arginine may be administered in an amount of about 10 mM, 25 mM, 50 mM, 75 mM, 100 mM, 125 mM, 150 mM, 175 mM, 200 mM, 200 mM, 225 mM, 250 mM, 275 mM, 300 mM, 325 mM, 350 mM, 375 mM, 400 mM, 425 mM, 450 mM, 475 mM, or 500 mM per day. In an embodiment, the nitric oxide synthase substrate is L-arginine and is administered by topical administration to the eye of the subject in need thereof in an amount from about 10 mM to about 500 mM twice daily, from about 50 mM to about 300 mM twice daily, from about 70 mM to about 200 mM twice daily or from about 100 mM to about 150 mM twice daily.

Agents may be administered in accordance with the present disclosure in the form of pharmaceutical compositions, which compositions may comprise one or more pharmaceutically acceptable carriers, excipients or diluents. In exemplary embodiments disclosed herein compositions may be administered as injectable solutions, in oral dosage forms or in a form or vehicle suitable for topical administration (such as eye drops, eye wash, ointment, gel or contact lenses).

Examples of pharmaceutically acceptable carriers or diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Pharmaceutical forms suitable for injectable use include sterile aqueous solutions (where water soluble) or dispersions and sterile powders for the extemporaneous preparation of sterile injectable solutions or dispersions. The formulation must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. Isotonic agents, for example, sugars or sodium chloride may also be used.

Sterile injectable solutions are prepared by incorporating the active agent in the required amount in the appropriate solvent with various of the other ingredients enumerated above, as required, followed by filter sterilisation. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique that yield a powder of the active ingredient plus any additional desired ingredient from previously sterile-filtered solution thereof.

Compositions may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active agent. The percentage of the compositions and preparations may, of course, be varied and may conveniently be between about 5 to about 80% of the weight of the unit. The amount of active compound in such therapeutically useful compositions is such that a suitable dosage will be obtained.

Tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active agent may be incorporated into sustained-release preparations and formulations.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations of any two or more of said steps or features.

The citation of any reference herein should not be construed as an admission that such reference is available as "Prior Art" to the present application. Further, the reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure is further described by reference to the following non-limiting examples.

EXAMPLES

Example 1—nNOS Expression in Myopic Eyes

The inventors investigated the expression of nNOS in amacrine and bipolar cells during the development of myopia and recovery from myopia induced with spectacle lenses in young guinea pigs.

Guinea pigs (*Cavia porcellus*, pigmented, tricoloured) were reared and housed with their mothers and littermates as previously described (McFadden et al., 2004; Howlett and McFadden, 2007). Animals were housed in litter lined plastic boxes (65×40×20 cm) with wire tops. Lighting was provided by overhead white light emitting diodes, with cyclic 12/12 hr light/dark conditions. The research was approved by the University of Newcastle Animal Care and Ethics Committee.

General Procedures

To induce different conditions of defocus, three different groups of guinea pigs were raised from post-natal (P) day 6 with a lens worn over one eye. Group 1 was raised with a −6D lens (n=5) from P6 to P16 to make them myopic. Group 2 was raised with a 0D lens (plano, n=4) over the same period as a control. Group 3 (n=4) was first made myopic with a −6D lens worn from P6 to P13, and then allowed to recover from their induced myopia by removing the lens for 3 days until P16. Refractive error and axial parameters were measured in both eyes (P16 in Group 1 and 2; P13 and P16 in Group 3). In all animals, untreated fellow eyes served as matched controls and data is expressed as the relative difference between the lens-wearing eye and the fellow eye.

Lenses

Concave lenses made of polymethylmethacrylate (diameter, 12 mm; Gelflex, Perth, Australia) were worn in front of the eye with an approximate distance of 5 mm from the cornea to the lens apex. Lenses were attached onto two arcs of Velcro®, glued above and below the eye while the animals were briefly anesthetized with halothane in oxygen. Lenses were attached onto the matching arcs the following day (P6). The lenses were replaced with clean lenses every day while animals were in the dark.

Refractive Error and Biometry Measures

Refractive error was measured by streak retinoscopy in hand-held, awake, cyclopeged animals, induced with 2-3 drops of 1% cyclopentolate hydrochloride (Cyclogyl™, Alcon). Spherical equivalent was calculated as the mean refractive error in the horizontal and vertical meridians.

Eye dimensions on the optic axis were measured by scan ultrasonography (20 MHz) in guinea pigs anesthetized with isoflurane (induction: 5%; maintenance: 1-2%; oxygen flow rate: 1 L/min). Procedures and peak selection have been previously described (McFadden et al., 2004, Howlett and McFadden, 2006). Ocular length was the axial distance from the anterior corneal surface to the back of the sclera.

Immunohistochemistry

Guinea pigs were anaesthetised with isoflurane in oxygen, euthanized by intraperitoneal injection of pentobarbital (40 mg/kg body weight), and their eyes enucleated. Eyes were dissected to remove the anterior portions and the resulting eyecups were fixed by immersion in 4% paraformaldehyde in 0.1 M phosphate buffer (PB), pH 7.4 for 2 hr. Following fixation, eyecups for vertical sections or retinas for whole mount were transferred to a 30% sucrose solution in PB for 24 hr at 4° C., then frozen using liquid nitrogen and stored at −70° C.

Prior to staining, eyecups or retinas were thawed, and transferred to 0.01 M phosphate buffered saline (PBS; pH 7.4). Fluorescence immunohistochemistry was carried out on vertical sections (40 μm vibratome or 15 μm cryostat sections) or whole mounts that were incubated in 10% normal donkey serum (NDS) and 1% TritonX-100 in PBS for 1 hr at room temperature to block the non-specific binding sites. Sections were then incubated at 4° C. (overnight for vertical sections or 4 days for whole mounts) with rabbit polyclonal antibody directed against nNOS (Sigma, dilution 1:10000 in PBS containing 0.5% Triton X-100). Tissue was washed in PBS for 30 min (3×10 min) and afterwards incubated for 2 hr at room temperature (sections) or for 3 days (whole mounts) with carboxymethylindocyanine (Cy3)-conjugated affinity-purified donkey anti-rabbit IgG (Jackson Immuno Laboratories, west Grove, dilution 1:500). The sections were washed for 30 min with 0.1 M PB and cover-slipped with Vectashield mounting medium (Vector Labs, Burlingame, Calif.).

Stained sections and whole-mounts where analyzed using a Leica TCS SP2 confocal laser-scanning microscope (Leica Microsystems, Wetzlar, Germany). Cy3 labelling was excited using the 543 nm line of a HeNe laser. Immunofluorescence images were processed in Leica TCS SP2-PC software.

Topographic Quantification and Isodensity Maps

The spatial densities of NOS type-I, NOS type-II and NOS-Displaced Amacrine Cells (ACs) were measured in retinal whole-mount preparations of each experimental group. NOS-bipolar cells were also counted in vertical sections from myopic animals. Whole-mounts were mapped systematically in 1 mm steps, using a calibrated eyepiece graticule. At these locations, serial optical sections were made through the retina, using a confocal microscope. By following each nNOS-immunoreactive cell at multiple depths, every cell was counted in the selected region once. For the density maps, fields of 600 μm×600 μm were sampled in 1-mm steps on the retina, in nasal, nasal-dorsal, dorsal, dorsal-temporal, temporal, temporal-ventral, ventral and ventral-nasal directions, with the optic disc at the centre. Retinal isodensity maps were generated with Sigma Plot 10.0 (Systat Software), each one plotted from 64 discrete regions.

Analysis

Cell-density measurements were expressed as mean±standard error (SE). Data is generally expressed as the difference between the treated and the fellow eye, unless otherwise specified. Statistical analysis reported was based on ANOVA and independent or paired sample Student's t-tests as appropriate. All statistical tests were performed using SPSS (SPSS for Windows V15.0).

Results

In the −6D group, eyes wearing a lens for 10 days became more myopic than the untreated fellow eyes (by −7.4±0.81 D, FIG. 1A). This myopia was much greater than that seen in the control 0D lens group (p<0.001) (FIG. 1A). In the recovery group, eyes wearing −6D lenses for 7 days also initially developed considerable relative myopia (−7.1±1.82 D). However, after 3 days of normal vision, there was no longer any difference between the recovery and the fellow eyes (−0.01±0.22 D) and their relative refractive error at P16 was far less myopic than the −6D group (p<0.001). Over the 3 days of recovery, the difference between the eyes changed by (+7.1±0.98 D, FIG. 1A). Therefore, hyperopic defocus (from a minus lens) caused a myopic shift, while myopic defocus (during recovery) caused a relative hyperopic shift in refractive error.

Wearing a −6D lens caused the eye to elongate relative to the fellow eye not wearing a lens (−6D group at P16, 106±22 μm; recovery group prior to −6D lens removal at P13, 91±33 μm). In contrast, the relative elongation caused by wearing a 0D lens was much less (19±51 μm) (FIG. 1B). Striking differences were found in the recovery group after the −6D lens was removed for 3 days. The prior elongation was lost, and instead the eye became shorter in length compared to its fellow eye (by −31±27 μm). The change in relative growth over the 3 days recovery period was −123±7 μm, FIG. 1B), significantly different to animals that continued to wear a −6D lens (p<0.01) Therefore, minus lenses made the eye grow, while eyes shrank during recovery from myopia.

In the inner retina, nNOS immunoreactivity was detected in three different types of amacrine cells (type-I, type-II and NOS-displaced amacrine cells (DACs)) and in one type of cone bipolar cell (data not shown). Type-I cells exhibited well immunostained somata located at the proximal border of the INL, with processes projecting at the level of s3 of the IPL. Their dendritic fields were wide and intensely ramified (data not shown). Somata of type-II cells were also located at the same level of the INL, but smaller in comparison and weakly immunostained. Their dendritic fields were narrower, and projected at the level of s1. NOS-DACs presented well immunostained somata at the GCL, with processes projecting at the level of s5 with narrow dendritic fields (data not shown). NOS-bipolar cells exhibited weak immunostained somata in middle areas of the INL. Unlike axon terminals, their dendritic arbors were properly labeled and connected with cone pedicles at the OPL (data not shown). This immunostaining pattern was consistent through all the experimental groups.

Figure 2:
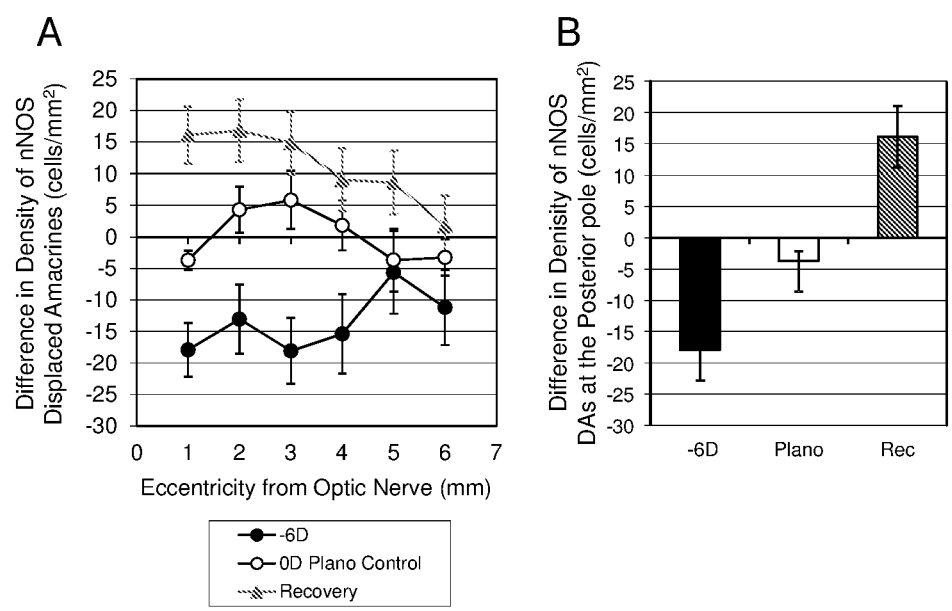
FIG. 2. Relative difference in density of nNOS-displaced amacrine cells in three treatment groups of guinea pigs in Example 1. A. Difference in density averaged for 8 radial sections across the retina at 1 to 8 mm from the optic nerve. B. Mean difference in density in central retina 1 mm from the optic nerve.

In all untreated eyes, the density of nNOS DACs varied across the retina, being highest in ventral retina (mean 141 cells/mm$^2$) and lowest in dorsal retina (mean 66 cells/mm$^2$) and density declined the greater the eccentricity from the optic nerve (119 cells/mm$^2$ at 1 mm and 79 cells/mm$^2$ at 6 mm). FIG. 2A shows the difference in density between the lens-wearing and fellow eyes of nNOS-DACs for each treatment group with increasing eccentricity. No significant changes occurred in animals wearing 0D lenses. However, in retinas from myopic eyes (−6D group), nNOS expression in DACs significantly decreased at 1, 2, 3 and 4 mm eccentricities from the optic nerve (average, −13%), with the largest decline in ventral retina. Exactly the opposite occurred during the recovery from myopia, where the density of nNOS DACs increased (average +14%), and the biggest increases again occurred closest to the optic nerve (FIG. 2A). The relative density differed significantly between the myopia and myopia recovery groups (RM 2 way ANOVA, $F_{(2,104)}=13.5$, p<0.001 at 1, 2, 3 mm and p=0.003 at 4 mm distances from the optic nerve). The difference in expression of nNOS in DACs in central retina (FIG. 2B) bears a striking resemblance to the difference in refractive error for each treatment group (FIG. 1A). Additionally, the changes in eye shape during myopia and myopia recovery occurred in opposite directions respectively, and in both cases, were also concentrated about the optic nerve where the density of nNOS expression was maximally changed.

A decline in cell density was not observed in the numerous nNOS bipolar cells counted blind in vertical sections between 1 and 4 mm from the optic nerve from a separate group of four myopic animals raised with −6D lenses (P16: −6D eye, 3028±472 cells/mm$^2$; fellow eye, 2875±432 cells/mm$^2$, p=0.06) showing that the decrease in nNOS in myopic eyes was restricted to specific cell populations.

The inventors have shown that the density of a specific amacrine cell type (nNOS displaced amacrine) changes its expression of nNOS depending on the sign of defocus experienced by an eye. Specifically, eyes which have been driven to become myopic and elongated by exposure to hyperopic defocus have reduced levels of nNOS expression, while eyes which inhibit their growth and shift in the opposite hyperopic direction as a reaction to myopic defocus, have increased levels of nNOS expression. These changes in refractive error, eye shape and nNOS expression are all concentrated in the posterior pole of the eye and are maximized around the optic nerve.

Example 2—Effect of Intravitreal Injection of L-Arginine on Form Deprivation Myopia in Guinea Pigs L-arginine is synthesised by NOS and is the precursor for nitric oxide. It is necessary for the biosynthesis of NO by all forms of NOS. Using intravitreal injections of L-arginine, the inventors sought evidence for a functional role for NO in form deprivation myopia development. NO has a short half-life of only seconds. Therefore, to keep eyes dosed with L-arginine for as long as possible during form deprivation and to avoid multiple injections, the inventors first developed a minimal paradigm in which form deprivation could be reliably induced over a short period.

Methods

Fifty-seven pigmented guinea pigs (*Cavia porcellus*) were sourced from the University of Newcastle and housed as described in Example 1. Animals were provided with food and water ad libitum and the room temperature was maintained at 22° C. The University of Newcastle under Australian legislative requirements approved all procedures.

Animals wore classical form diffusers made of translucent moulded Perspex (0.8 mm thickness, 24% transmission) on their right eyes. Diffusers were mounted onto plastic washers backed with Velcro® and attached to mating Velcro® arcs which were affixed above and below the eye.

Animals were assigned to one of seven treatment groups (Table 1). From seven days of age, five of these groups were form deprived in the right eye for 3 days with a diffuser (two groups wore no diffusers and served as controls for form deprived animals). Six groups of animals were intravitreally injected with either L-arginine or physiological saline once per day, just before lights came on at 10 am. One group wore diffusers, but received no injection as a control. At ten days of age, cycloplegia was induced in all animals and refractive error and ocular components were measured. Two retinas, one a saline control and another that had been injected with the highest dose of L-arginine, were analysed by histochemistry for morphological markers of L-arginine induced toxicity.

Ocular length and axial components were also determined as described in Example 1.

Over a period of three days, two animals received daily 10 µl intravitreal injections of either physiological saline or L-arginine (9.3 mM) in one eye, similar to the primary experiment. Animals were anaesthetised (1.5% isoflurane in oxygen) before they were euthanized with Sodium Pentobarbitone (0.5 ml/gm; i.c.; Virbac laboratories). Eyes were then enucleated and prepared for histochemistry. Only the injected eye from each animal was analysed. The cornea, anterior chamber and lens were removed. Eyecups were fixed in 4% paraformaldehyde for two hours at 4° C. Eyecups were stored in 30% sucrose (in phosphate buffer, PB) at 4° C. for three days, before being immersed in a mould containing optimum cutting temperature compound (Tissue-Tek® OCT™). Eyecups were frozen within two minutes of being immersed in OCT and 15 µm vertical sections were cut on a cryostat (Leica CM1850). Sections were then stained with 0.5% cresyl-violet for 5 minutes, before being washed in phosphate buffered saline (PBS) three times. Sections were then mounted with Vectashield® mounting medium (H-1000). Images were taken (Zeiss Axio Scope A.1 with Axiocam MRm) at 20× magnification with 1260×1024 picture resolution and an exposure time of four seconds.

The data presented are means±standard errors of the mean. All figures and statistics are based on the difference between the lens-wearing eye and the fellow non lens-

TABLE 1

Treatment groups. Drug delivery method is described by treatment group. Form diffusers were worn on one eye only and all injections were 10 µl. L-arginine dosage was calculated as weight per injection, molarity in syringe and molarity in the eye. N refers to the number of animals used per treatment.

| Monocular Treatment | Injection Type | L-Arginine weight per injection (µg) | L-Arginine molarity in syringe (mM) | Estimated L-Arginine concentration in the vitreous (nM) | N | In-text reference group |
|---|---|---|---|---|---|---|
| FD | NIL | NIL | NIL | NIL | 8 | FD NIL |
| FD | 10 µl Saline | 0 | 0 | 0 | 8 | FD 0 mM |
| FD | 10 µl Saline | 9 | 5 | 0.4 | 9 | FD 0.4 mM |
| FD | 10 µl Saline | 52 | 30 | 2.2 | 11 | FD 2.2 mM |
| FD | 10 µl Saline | 218 | 125 | 9.3 | 9 | FD 9.3 mM |
| NIL | 10 µl Saline | 52 | 30 | 2.2 | 6 | 2.2 mM |
| NIL | 10 µl Saline | 0 | 0 | 0 | 6 | 0 mM |

To establish the size of the guinea pig vitreous, and thus the molarity of the substrate within the eye, ten vitreous chambers were extracted from ten eyes. The volume of the vitreous was 125 µl. Based on this, three drug doses of L-arginine were employed: low (0.4 mM), medium (2.2 mM) and high (non-toxic: 9.3 mM) (See Table 1). A 30 gauge Hamilton syringe was used to slowly inject into the vitreous through the temporal sclera of right eyes, approximately 2 mm posterior to the limbus. All injections were 10 µl of either physiological saline (0.9%) or L-arginine dissolved in saline (pH 7.4 for all injections).

Cycloplegia was induced as described in Example 1, and refractive error subsequently measured as described in Example 1.

wearing eye and are referred to as relative refractive error and relative ocular distances. Statistical comparisons between lens wearing groups were based on one way ANOVAs followed by Holm-Sidak post hoc tests to account for family-wise error. Correlations were based on Pearson's regression analysis. Statistical analysis used Prism®, Graph Pad Software, Inc. V 6.

Results

There was no difference in relative refractive error between the two groups that were not form deprived (difference: −0.2D, p=0.46), despite one receiving a mid dose of L-arginine (2.2 mM), and the other vehicle only. This indicates that a moderate dose of L-arginine alone did not influence the refractive error of the eye.

Figure 3:
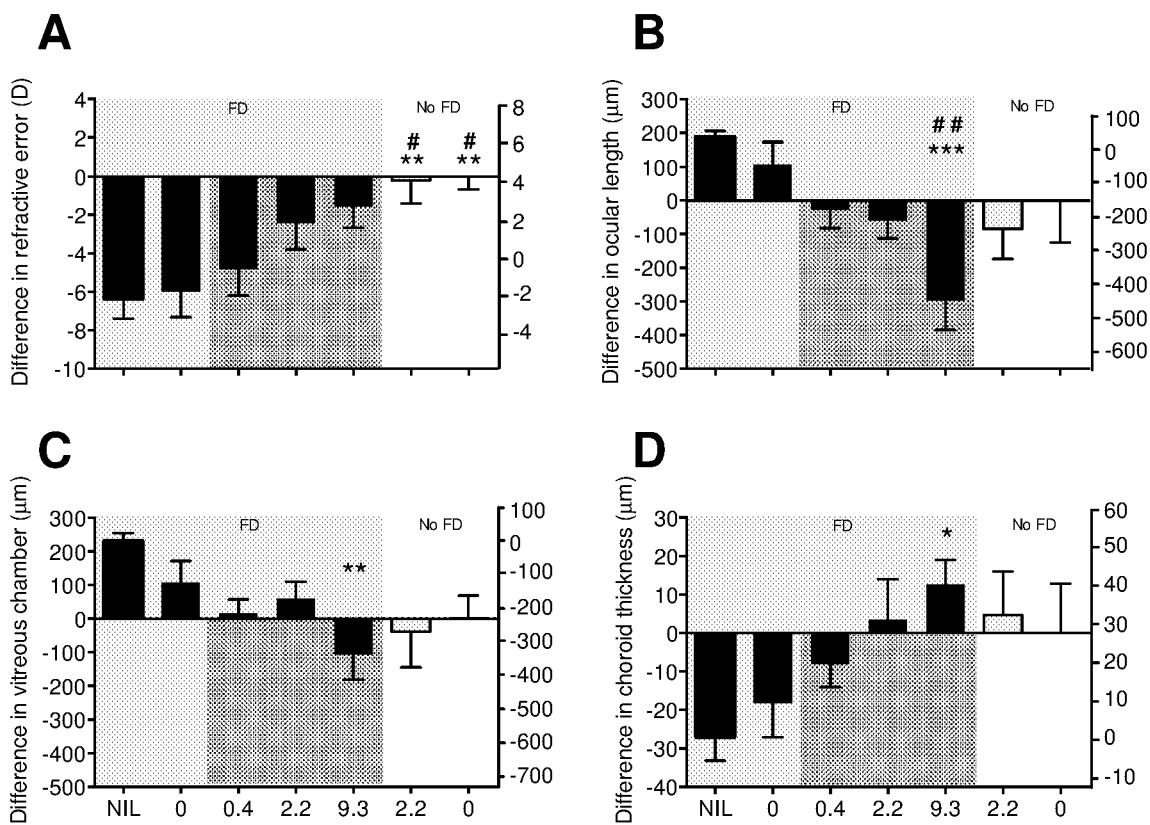
FIG. 3. The effect of intravitreal administration of L-arginine on form deprivation (FD) myopia in different groups of guinea pigs in Example 2. The first 5 groups were form-deprived in one eye for 3 days (dark shading), and the last 2 groups were not form-deprived (light shading). A daily intravitreal injection was made into the eye wearing the diffuser (or in one eye in animals not given FD). Stipled background shading indicates those three groups that received injections of L-arginine during FD. The x-axis shows the concentration estimated in the vitreous in mM of L-arginine. "0" means vehicle injections without L-arginine. The data shows the difference between the two eyes (light shading). A. Difference in refractive error in diopters (D), $F(6.39)=4.48$, $p<0.01$. B. Difference in ocular length $F(6.55)= 4.82$, $p<0.001$. C. Difference in vitreous chamber depth $F(6.55)=3.20$, $p<0.01$. D. Difference in choroid thickness $F(6, 56)=2.43$, $p=0.04$. $*p<0.05$, $p<0.01$, $*p<0.001$ refers to significant differences relative to the FD NIL group. $\#p<0.05$, $\#\#p<0.01$, $\#\#\#p<0.001$ refers to significant differences relative to the FD 0 group.

Form deprivation induced relative myopia in animals that received no injections (FD NIL) or vehicle injections (FD 0 mM), the latter being −5.98 (p=0.029) more myopic than controls that had no form deprivation, but received vehicle injections only (0 mM) (FIG. 3A). The degree of relative myopia present in eyes that had form deprivation only (FD NIL) or form deprivation combined with vehicle injections (FD 0), was greater than in all other treatment groups. Importantly, animals that had form deprivation and were injected with L-arginine (FD 2.2 mM, FD 9.3 mM) were not significantly different from animals that had no form deprivation FIG. 3A). As the L-Arginine dose increased, less relative myopia occurred in response to form deprivation, and refractive error became relatively more hyperopic ($R^2$=0.15, p=0.030).

Similar to refractive error, ocular length (FIG. 3B) was not affected by L-arginine when eyes were not form deprived (the difference between groups was 83 μm, p=0.44). Corresponding with refractive error, ocular length was greater in eyes that had form deprivation only (FD NIL) compared with all other treatment groups. Form deprivation combined with a high a dose L-arginine (FD 9.3 mM) caused the eye to shorten the greatest amount (by −484 μm; p<0.001; FIG. 3B). Importantly, ocular length in animals that had form deprivation and were injected with vehicle only (FD 0 mM) was 403 μm (p<0.001) greater than in animals that had form deprivation and were injected with a high dose of L-arginine (FD 9.3 mM). As the L-arginine dose increased, so did the extent of ocular growth inhibition ($R^2$=0.33, p<0.001).

Vitreous chamber depth (FIG. 3C) was associated with ocular elongation ($R^2$=0.28, p<0.001). Thus, vitreous chamber depths in animals that had form deprivation only (FD NIL), were relatively longer compared with those of all other treatment groups, and were 484 μm longer than that of animals that had form deprivation combined with a high a dose L-arginine (FD 9.3 mM, p<0.001; FIG. 3C). Similarly, animals form deprived and given vehicle injections (FD 0 mM) expanded their vitreous chambers, while animals that had form deprivation combined with a high dose of L-arginine (FD 9.3 mM) showed relative shrinkage, although this difference did not reach significance (215 μm, p=0.12; FIG. 1C). Thus, similar to ocular length, as the L-arginine dose increased, so did the extent of vitreous inhibition ($R^2$=0.15, p=0.012).

It can be seen in FIG. 3D that choroids were thinner in eyes that had form deprivation only (FD NIL), compared with those of other treatment groups. Similar to vitreous chamber changes, the greatest differences (−39 μm; p=0.03) occurred between animals that only had form deprivation (FD NIL) and animals that had form deprivation and high a dose L-arginine (FD 9.3 mM). Animals that had form deprivation and were injected with vehicle only (FD 0 mM) had choroids that were 31 μm thinner than animals that had form deprivation and were injected with a high dose of L-arginine (FD 9.3 mM), although this did not reach significance (p=0.14). Accordingly, as the L-arginine dose increased, so did choroid thickness ($R^2$=0.13, p=0.014).

The inventors then examined the morphology of two retinas, one from an eye that had an intravitreal injection of saline only and another that had the highest intravitreal dose of L-arginine (9.3 mM). Both retinas appeared normal, with no evidence of degeneration of photoreceptors, necrosis or gliosis, indicating three days of the highest dose of L-Arginine had no gross effect of toxicity on the retina (data not shown).

The inventors have thus shown that the intravitreal administration of L-arginine inhibits the relative myopia normally brought about by form deprivation. The response was dose dependent and observed across refractive error and multiple ocular components, namely, vitreous chamber depth, choroid thickness and ocular length.

Example 3—Effect of Intravitreal Injection of L-Arginine on Lens-Induced Myopia in Guinea Pigs As described in Example 1, the inventors have shown that nNOS is down regulated in eyes that become myopic in response to negative lenses. The inventors therefore sought to determine if this down-regulation during negative lens-wear may be able to be reversed, thereby inhibiting myopia, by injecting into the eye L-arginine, a precursor for the production of nitric oxide.

Methods

Young guinea pigs (pigmented variety, *Cavia porcellus*) were raised with their mothers as described in Example 1. Lighting was provided as described in Example 2. The research was approved by the University of Newcastle Animal Care and Ethics Committee.

Two experimental protocols were used. In Experiment 1, young guinea pigs were randomly divided into three drug treatment groups: no injection (n=14), vehicle (n=14) and 0.2 mM L-arginine (n=16). Animals in the latter two groups received a daily 10 μl intravitreal injection in one eye at 7, 8 and 9 days of age (Table 2). At 7 days of age (and immediately after the ocular injection in the injected groups) all guinea pigs had a −6D lens attached over one eye for 3 days to induce myopic growth. The fellow eye was untreated. At 10 days of age, the −6D lens was removed, animals were cyclopleged and refractive error was measured in both eyes. In Experiment 2, sixteen guinea pigs received an intravitreal injection of either vehicle (n=8) or 0.2 mM L-arginine (n=8) into their untreated eye at 16 days of age (Table 2). Injections were made 1 hour after the beginning of their 12 hr light cycle. 3 hours after injection, light adapted animals were euthanized, and the injected eye removed and processed using immunohistochemistry.

TABLE 2

Experimental Design. N, number of animals in each group. Dose shown is the estimated dose at the level of the retina. LA, L-arginine.

| Experiment | Drug Treatment | Time of Injection | Optical Treatment | Measure | N |
|---|---|---|---|---|---|
| 1 | No Injection Vehicle 0.2 mM LA | 7, 8, and 9 days of age | −6D lens on one eye from 7-10 days of age | Refractive Error at 10 days of age | 14 14 16 |
| 2 | 0.2 mM LA Vehicle | 15 days of age | Nil | nNOS expression 3 hrs after injection | 8 8 |

To induce myopia, −6D lenses (PMMA, 12 mm in diameter, posterior curvature 8.5 mm, Gelflex®, Perth Wash.) were attached as described in Example 1. At 7 days of age, the lens was attached to the arcs, ensuring that the lens was centered on the eye. The lens was replaced with a clean lens daily, just before the commencement of the light cycle, under a dim red light (guinea pigs are insensitive to red light).

To make the L-arginine (LA), 217.75 mg of LA (Sigma, A5006) was added to 10 ml of isotonic saline (Pfizer) to create 125 mM fresh stock each day. Hydrochloric acid was used to lower the stock to a pH of 7.4. The stock was diluted with isotonic saline to produce a final dose of 0.185 mM of LA (~0.2 mM) at the level of the retina based on a vitreous volume of 125 µl and an injection volume of 10 µl. Vehicle injections consisted of 10 µl of isotonic saline (pH 7.4).

Guinea pigs were briefly anaesthetised with isoflurane in oxygen and intravitreal injections were made through the pars plana ~1 mm posterior to the limbus at an angle of approximately 40° to avoid contact with the crystalline lens and retina. Drugs were delivered using a 0.3 ml syringe (Diabetic BD UltraFine II) with a 31 gauge needle. After the injection, antibiotic gel (Conoptal) was applied lightly to the cornea, and animals recovered rapidly in a warm darkened box.

Shortly before the light cycle commenced, animals were cyclopleged in the dark with 2 drops of 1.0% cyclopentolate hydrochloride solution (Alcon, Australia) applied to the cornea for 1 min to each eye. After 1.25 hours, the refractive error was measured at the centre of the pupil using a Nidek Auto Refractometer (AR-20, Nidek Co., Japan). Each output was the average of 10 responses, which was repeated at least six times. Data is presented as the spherical equivalent refractive error, and is the average of these 6 recordings.

In Experiment 2, three hours after their intravitreal injection, animals were anaesthetised with isoflurane in oxygen and then euthanized with an intraperitoneal injection of sodium pentobarbitone (160 mg/kg; Lethabarb) into the heart. The eye that had received treatment was then enucleated. The top of the eye was dissected around the limbus, and the cornea, anterior chamber and lens removed. The remaining eyecup was fixed in 4% paraformaldehyde in 0.1 M PBS for two hours at 4° C., rinsed thoroughly in PBS, cryoprotected in a 30% sucrose solution for two nights at 4° C., and then stored at −80° C. until used.

Eyecups were thawed at room temperature. An incision at the nasal location was made to help orient the retina for later imaging. The vitreous was removed and the retina was teased off of the eyecup using a fine donkey-hair brush, and severed at the optic nerve using a rounded spatula. A further three small incisions were made at the temporal, dorsal and ventral locations, to help the retina lie flat for whole mounting. Retinas were then stored in individual vials of phosphate buffered saline (PBS, 0.1M).

Retinas were pseudo randomly divided into three groups, to allow adequate time for imaging and cell counting. The retinas were placed in a well plate and washed in PBS for 3×10 minutes. The retinas were then treated with 0.5% Triton X-100 for 40 minutes and then washed in PBS a further 3×10 minutes to remove the Triton. Normal Donkey Serum (1:10 PBS, Jackson) was used for blocking for one hr at room temperature. Then, the primary antibody for nNOS (Rabbit brain 1:10000 PBS, 1:10 Normal Donkey Serum; Sigma, N7280) was applied and immersed whole mounts were mixed (Ratek Platform Shaker OM1) for one hr at room temperature. The retinae were then incubated in primary antibody for three nights at 4° C. The retinae were then placed on the mixer at room temperature for a further 30 minutes, and then washed in PBS 3×10 minutes. The retinae were placed in a secondary antibody (donkey anti rabbit 1:500, Jackson, 7/1-545-152) for one hr at room temperature and then placed in 4° C. for two nights. Finally, retinae were kept at room temperate for 30 minutes, washed in PBS 3×10 minutes and mounted onto Superfrost slides, ganglion cell layer facing upwards. Vectashield mounting medium was used prior to covering with a glass cover slip.

Photographs were taken using a fluorescent microscope (Zeiss, Axioscope A1) along each of eight radii centred on the optic nerve head. The stage was moved at 1 mm intervals, to allow samples every mm along each of the radii. Images were taken at 20× magnification. Image J (National Institutes of Health) was used for cell counting. The retinal neurons counted were nNOS displaced amacrine cells and NOS Type I cells. Cell numbers were converted to density per 1 $mm^2$ based on a conversion factor of 0.1975.

Statistical analyses were generated using SPSS Statistics 21 and SigmaPlot (V 11, 2008 Systat Software).

For biometric data analysis, data is presented as averages for each eye and as the average difference between the two eyes (the interocular difference, IODs) together with the standard error of the mean. Two-way ANOVAs were used to determine whether the differences between the treated and untreated fellow eye were significant for each of the three injection groups. A one-way ANOVA was used to determine whether there were significant differences between the IODs between the eyes for the 3 groups. Post hoc comparisons used the Holm-Sidak method to control for family wise error.

For cell count data analysis, data is presented as the mean density of cells per $mm^2$ in two ways for each cell type measured: (i) averaged at each eccentricity (collapsed over each orientation) and (ii) averaged at each orientation (collapsed over eccentricity). Two-way ANOVAs for each cell type were used to determine if treatment groups were significantly different. Holm-Sidak comparisons were used to determine whether these differences between groups were significant at each eccentricity and at each radii orientation.

Results

Figure 4:
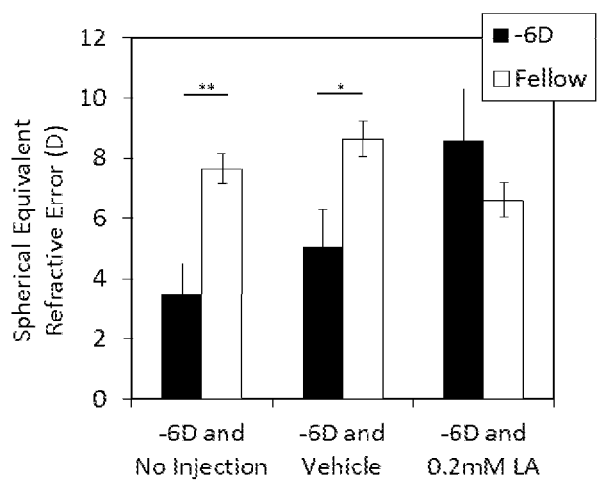
FIG. 4. Refractive changes after 3 days of −6D lens wear in three treatment groups (Example 3). A. Spherical equivalent mean refractive error in the −6D lens wearing eye and the untreated fellow eye in each group. D, diopters. *, $p<0.05$; $p<0.01$ from Holm-Sidak comparisons after two-way ANOVA. B. Average interocular differences in spherical equivalent refractive error between the two eyes in each group. D, diopters. , $p<0.01$ from Holm-Sidak comparisons after one-way ANOVA.
Figure 4:
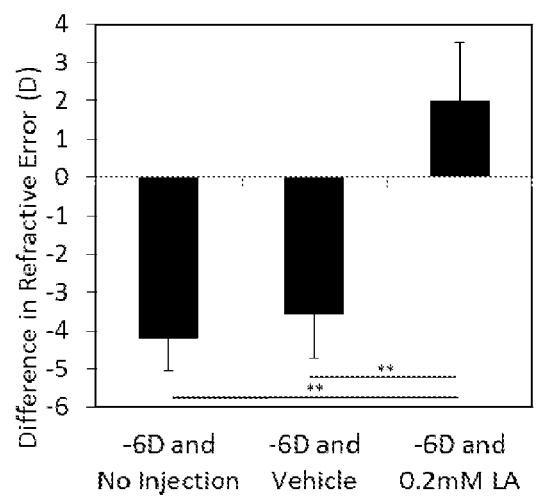

Guinea pigs are born with a positive refractive error (hyperopia) and the ocular growth increases during early development, so that the refractive error reduces towards zero (emmetropia). For animals that did not receive any injections, the −6D eye emmetropized more rapidly and was less hyperopic than the fellow eye after 3 days of lens wear (−6D eye: +3.48D Vs. fellow eye: +7.66D, FIG. 4A). This relative myopic IOD in refractive error was significant (−4.18D, t=2.724, p=0.008, FIG. 4A). Similarly, for animals which received vehicle injections, the −6D eye also developed relative myopia (−3.56D, t=2.323, p=0.023, FIG. 4). The IOD in mean refractive error was not significantly different between these two control groups (t=0.343, p=0.733, FIG. 4B).

In contrast, animals which had been injected with the L-arginine, failed to develop any relative myopia in the lens-wearing eye, instead becoming slightly more hyperopic by 2.00D, and there was no significant IOD in refractive error between the eyes (Holm-sidak, t=1.389, p=0.169, FIG. 4A). The mean IOD in refractive error for the 0.2 mM LA group was significantly different to the relative myopia that developed in both the non-injected control group (t=3.553, p=0.003, FIG. 1B), and the Vehicle injected group (t=3.199, p=0.005, FIG. 4B). The power of this test with alpha was calculated to be 0.913.

NOS displaced amacrine cells (DACs) were approximately 7 µm in soma diameter and were located in the ganglion cell layer, just below layer five of the inner plexiform layer (IPL) in the retina as described in Example 1 (data not shown). They were smaller than nNOS type I cells, with a much higher density. nNOS Type I cells were located in layer S3 of the IPL, with dendritic branches radiating away from the cell body as described in Example 1 (data not shown).

As shown in Example 1, the density of both cell types was higher towards the centre of the retina, compared to the peripheral retina, and substantially declined as peripheral eccentricity increased. Between 1 mm and 5 mm of eccentricity, cell density declined by 27.57 cells/mm$^2$ for the nNOS DACs (t=7.136, p<0.001) and 5.78 cells/mm$^2$ (t=6.70, p<0.001) for nNOS Type I. However, the two cells types differed in their radial distribution patterns. The nNOS DACs were much denser in the ventral retina and lower in dorsal retina (mean difference of 45.06 cells/mm$^2$, t=10.077, p=<0.001, FIG. 5B). In contrast, there was no significant difference in nNOS Type I cells density between different radial positions (FIG. 5D).

Figure 5:
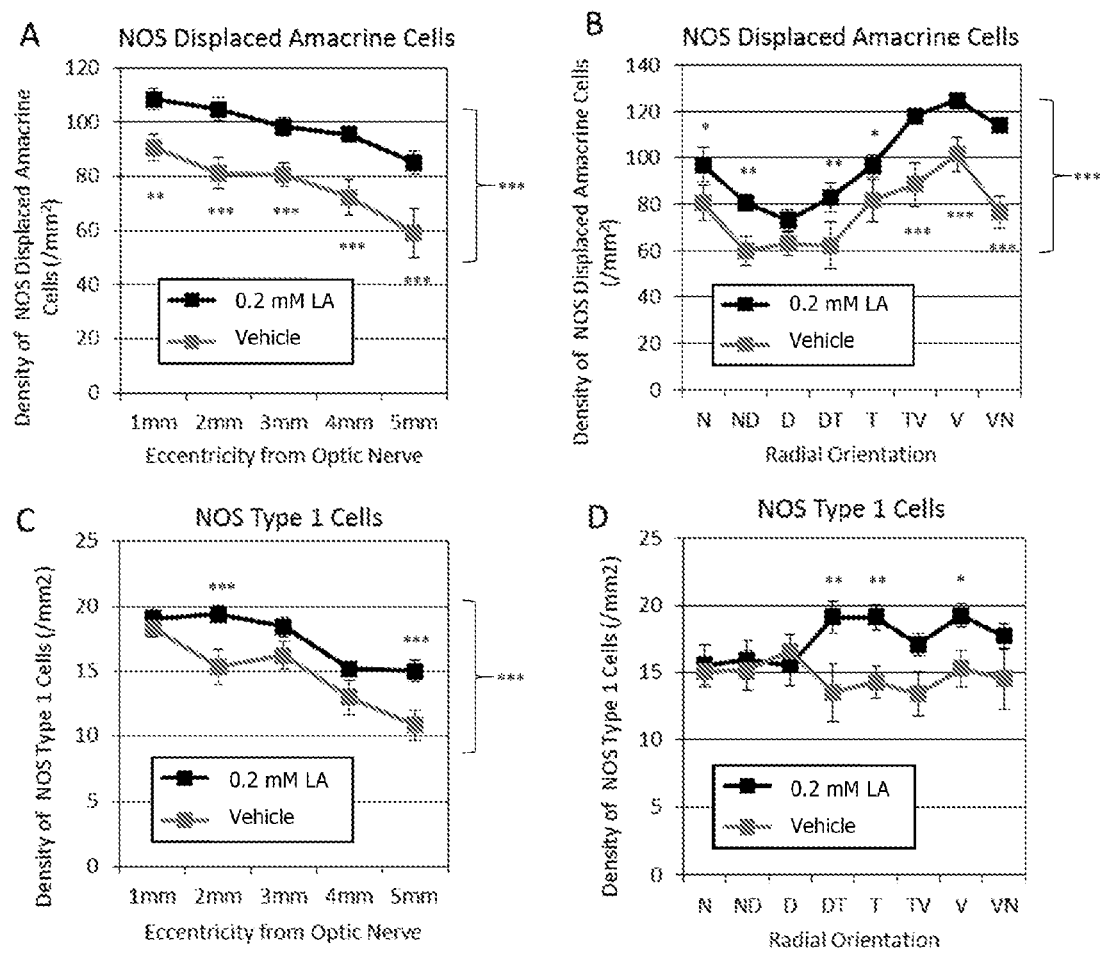
FIG. 5. Density of NOS displaced amacrine cells and NOS type I cells at different eccentricities and radial positions on the retina after intravitreal injection of 0.2 mM L-arginine (LA) and Vehicle (Example 3). A. Density of NOS displaced amacrine cells ($/mm^2$), at 5×1 mm intervals from the optic nerve. B. Density of NOS displaced amacrine cells ($/mm^2$), at 8 radial orientations around the retina. C. Density of NOS type I cells ($/mm^2$), at 5×1 mm intervals from the optic nerve. D. Density of NOS type I cells ($/mm^2$), at 8 radial orientations around the retina. N, Nasal. ND, Nasal-Dorsal. D, Dorsal. DT, Dorsal-Temporal. T, Temporal. TV, Temporal-Ventral. V, Ventral. VN, Ventral-Nasal. *, $p<0.05$; $p<0.01$; $*p<0.001$ from Holm-Sidak comparisons after two way ANOVA.

At each eccentricity from the optic nerve, the LA injected eyes had a significantly higher density of NOS displaced amacrine cells (DACs) than the vehicle injected eyes (F(4, 639)=14.433, p=<0.001, Power=1.0, FIG. 5) showing that injections of nNOS had upregulated its expression in nNOS DACs. This up-regulation was also observed at most radii positions (F(7, 639)=26.694, p<0.001, FIG. 5B).

The LA injections caused a significantly higher density of Type I amacrine cells expressing nNOS compared to the vehicle injected group (F(4, 639)=16.133, p=<0.001, Power=0.99, FIG. 5C). Unlike NOS displaced amacrine cells, this up-regulation was not present at all eccentricities, but reached significance for both 2 mm and 5 mm eccentricities (FIG. 5A). Differences were found in the Dorsal-Temporal (t=2.895, p=0.004), Temporal (t=3.052, p=0.002) and Ventral (t=2.035, p=0.042) radial orientations (FIG. 5D).

The results described above demonstrate that a single injection of L-arginine increased the expression of nNOS in the retina by approximately 20%. Additionally, increasing nNOS expression in the retina by intravitreal injections of L-arginine can inhibit the development of lens-induced myopia.

Given that in Example 1, nNOS expression was up-regulated when the eye was inhibiting its growth during the recovery from myopia, the inventors also examined the effect of reversing the upregulation of nNOS using a specific inhibitor of nNOS, N-w-propyl-L-arginine (nωPLA). That is, if up-regulation of nNOS was causal in the myopic recovery response, injections of nωPLA would be expected to inhibit the ability of the myopic eye recover from myopia.

In this second experiment, thirty four guinea pigs were raised and measured as described in Example 1. To induce myopia, animals wore a −6D lens on one eye from P6-P13, which was then removed for 3 days to initiate recovery from myopia, exactly as described in Example 1, Group 3. During the recovery period, animals received daily intravitreal injections (10 μl into the eye which had worn the lens) of either 6 mM nωPLA (PLA, n=9) or vehicle (0.9% isotonic saline, pH 7.4, n=11) on postnatal days P13, P14, and P15. To study the effect of the drugs on normal growth, a further seven animals were raised for the same period without lenses, and from P13 received a vehicle injection into the left eye and a 6 mM nωPLA injection into the right eye for 3 days. The dosage level of 6 mM refers to the concentration of nωPLA in the syringe. (Considerably smaller doses would be experienced at the level of the retina). In all animals, refractive error and axial parameters were measured in both eyes before and after the recovery period, at P13 and P16. In lens-wearing animals, untreated fellow eyes served as matched controls and data is expressed as the relative difference between the lens-wearing eye and the fellow eye.

Figure 6:
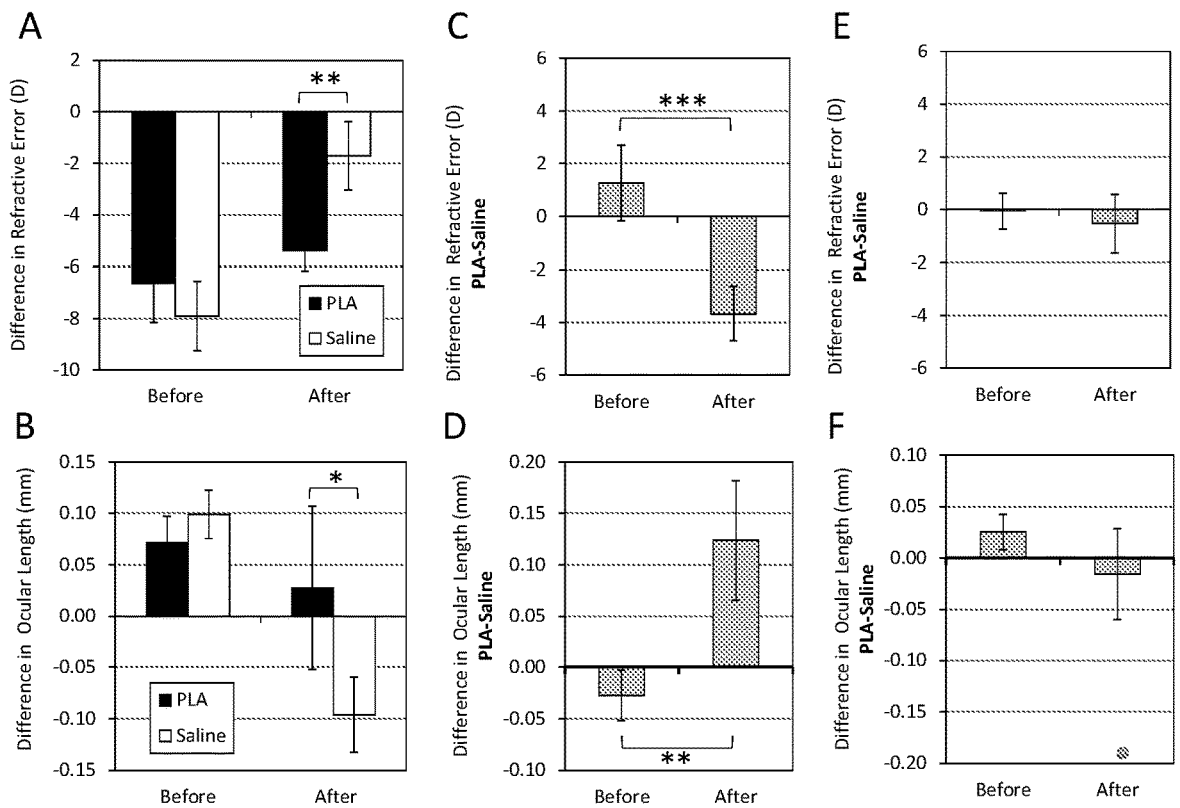
FIG. 6. Effects of intravitreal injection of 6 mM nωPLA on recovery from myopia (A-D) and on normal growth (E-F). Top row (A,C,E) shows refractive error. Bottom row (B,D,F) shows the corresponding ocular length. Data is taken from the difference between the lens-wearing eye and the fellow eye. Before refers to time P13 at the end of the −6D lens-wear period (A-D) or at the same age in animals not wearing lenses (E-F). After refers to time P16, 3 days after lenses were removed or at the same age in animals not wearing lenses. The leftmost panel (A, B) shows the effect of nωPLA and saline injections separately. The middle and rightmost panels (C-F) show the relative difference between nωPLA and saline groups and the mean standard errors of the two.

Both groups wearing −6D lenses developed similar amounts of relative myopia and increased eye lengths after 7 days of lens wear (PLA vs. Saline: −6.6 D vs. −7.9 D and +71 μm vs. +99 μm, respectively, FIG. 6A,B). The differences between these two groups before the recovery period (FIG. 6C,D) was not significant. After the three day recovery period, animals injected with saline recovered from their myopia (FIG. 6A) by reducing their eye elongation rate in the treated eye (FIG. 6B), while animals injected with PLA did not recover and remained significantly myopic (maintaining a difference between the eyes of −5.4 D, FIG. 6A). Relative to the saline group, PLA animals were more myopic after the recovery period (FIG. 6C) and had longer eyes (FIG. 6D).

The inhibition of recovery from lens-induced myopia by the specific nNOS inhibitor, nωPLA, was not due to a non-specific growth effect. In animals without myopia, nωPLA had no influence on either causing relative myopia (FIG. 6E) or in enhancing elongation over an identical period (FIG. 6F). Therefore, inhibiting nNOS in the eye specifically interfered with the ability of the eye to respond to myopic defocus and to inhibit its growth accordingly.

Example 4—Oral Administration of L-Arginine to Guinea Pigs

In this study, doses of L-arginine similar to those administered to humans for the treatment of cardiovascular conditions, were administered orally to guinea pigs to determine the effect on myopia. To induce myopia, the well established technique of form derivation (FD) was used.

Methods

Guinea pigs (pigmented variety, *Cavia porcellus*) were bred, housed, and raised as described in Example 1. The University of Newcastle Animal Care and ethics Committee approved all procedures.

Two experimental protocols were employed (Table 3). In Experiment 1, 12 animals wore a diffuser over one eye (form-deprivation, FD) for 7 days from 6-13 days of age. This period reliably induces myopia in the deprived eye compared to the untreated fellow eye. Seven of these animals also concurrently received a single gavage of L-arginine (200 mg/kg/day) each day at 9:30 am while briefly anaesthetised.

Given the short half-life of nitric oxide (NO) production in the retina (Szabo & Thiemermann, 1995), a single drug application may not be sufficient. Therefore, in Experiment 2, LA was given twice daily to keep the retina more consistently dosed with NO substrate. In order to limit the number of gavage procedures, we reduced the FD period to 3 days. In Experiment 2, 21 guinea pigs wore a diffuser over one eye for 3 days from 3-6 days of age. During the FD period, the following treatments were given at 9:30 am and 3:30 μm each day for 3 days. Control groups were given either no gavage or a gavage with distilled water twice daily. The experimental group received a physiological dose of L-arginine (25 mg/kg twice daily). All group details are shown in Table 3.

TABLE 3

Experimental Design.

| Experiment | Group Name | Drug Treatment | Form Deprivation (FD) | FD Age (days) | N |
|---|---|---|---|---|---|
| 1 | FD7 | Nil | FD for 7 days in one eye | 6-13 | 5 |
| | FD7 + LA 200 | Fed L-arginine (200 mg/kg once daily) | | | 7 |

TABLE 3-continued

Experimental Design.

| Experiment | Group Name | Drug Treatment | Form Deprivation (FD) | FD Age (days) | N |
|---|---|---|---|---|---|
| 2 | FD3 | Nil | FD for 3 days in one eye | 3-6 | 6 |
| | FD3 + Water | Fed Distilled H$_2$O twice daily | | | 8 |
| | FD3 + LA 50 | Fed L-arginine (25 mg/kg twice daily) | | | 7 |

At the end of the FD period, at 12 days of age (Experiment 1) or at 6 days of age (Experiment 2), after the morning gavage treatment, both eyes were cyclopleged and 1.25 hours later, refractive error was measured. Animals were then anaesthetised with gaseous anaesthetic (1% isoflurane in oxygen) and biometry measures were taken in both eyes with high frequency ultrasound as described in Example 1.

Form deprivation was achieved by attaching opaque diffusers to matching Velcro arcs glued above and below the experimental eye as previously described (Howlett and McFadden, 2006). Diffusers were checked every day twice a day to ensure they were clean and securely attached.

Animals were weighed each morning to calculate drug amounts. L-arginine (Sigma-Aldrich, 174.2 g/mol) was diluted with distilled water (not ionized) to a maximum volume of 0.5 mls per gavage. Control animals were gavaged with the same volume of distilled water only. Animals were anaesthetized with gaseous anaesthetic (1.5% isoflurane in oxygen) and were orally fed drug or vehicle solution directly into the stomach via the oesophagus using a 1 mm ball tip gavage needle. The procedure takes less than 1 min, and animals recover from the gaseous anaesthetic after several mins.

After cycloplegia was induced, refractive error was measured in each eye using streak retinoscopy as previously described (Howlett and McFadden, 2007; McFadden et al., 2004). The spherical equivalent was calculated as the average of the horizontal and vertical meridians (see Howlett and McFadden, 2006). Next, ocular length was measured using high frequency ultrasound (20 MHz) as previously described (McFadden et al, 2004). At least 20 traces were recorded for each eye and distances were averaged for at least 10 of these recordings. Peaks from the recordings were selected for the back of the cornea, the crystalline lens, and the vitreous chamber, and the layers at the back of the eye: the retina, choroid, and sclera. Ocular length was defined as the summed measurement from the front of the cornea to the back of the sclera.

Differences between the two eyes were analysed by repeated T-tests. The mean of calculated differences between the two eyes is referred to as relative myopia or relative ocular length. In Experiment 1, these relative differences were compared using one-tailed independent T-tests, and in Experiment 2, using one-way ANOVA (IBM SPSS Statistics 21).

Results

Experiment 1: Effect of Daily Feeding of
L-Arginine (200 mg/kg) on Myopia and Ocular
Length FD induced significantly more myopia in the FD eye compared to its fellow eye in the control group (FD7, t=6.4, p<0.001) but not in the animals also fed the drug L-arginine (t=2.0, p=0.05, FIG. 7A). The average relative myopia (FD eye-fellow eye) also differed between the two groups (p=0.005, FIG. 7C). Less relative myopia developed in the animals treated with FD and L-arginine than in the control animals (reduction of +5.1D or 72%, FIG. 7B).

Figure 7:
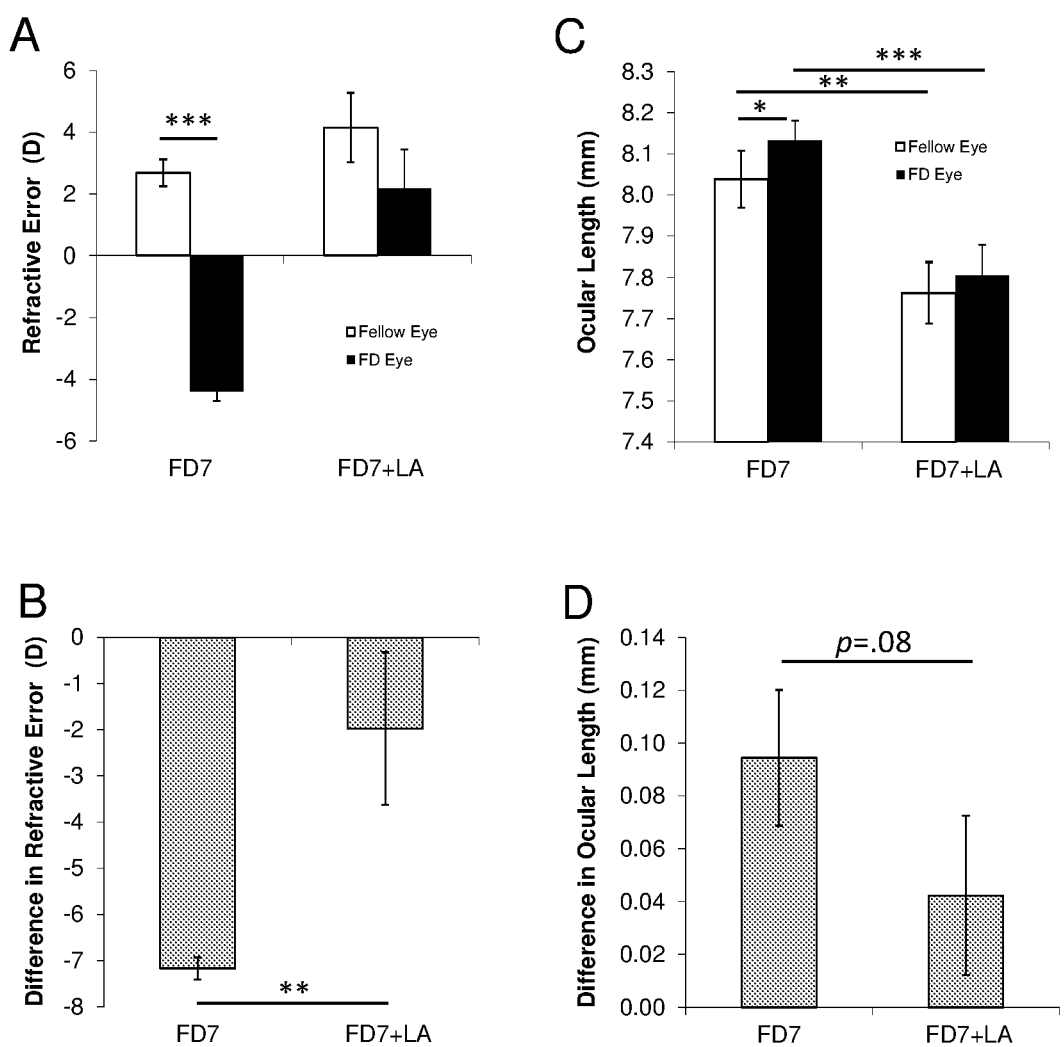
FIG. 7. Effects of daily feeding 200 mg/kg of L-arginine (FD7+LA) on 7 days of form deprivation (FD) in Experiment 1 (Example 4). Only one eye received FD. A. Refractive Error in each eye after 7 days of FD. B. Difference in Refractive Error between the eyes. Negative values indicate relative myopia in the FD eye. LA inhibits myopia. C. Ocular length in each eye after FD. Note that both eyes are smaller after feeding the drug. D. Difference in Ocular length between the eyes. Myopic eyes are relatively larger, while LA reduces the growth enhancing effects of FD, despite the fact that both eyes are also smaller due to the systemic administration of the drug through feeding.

The myopic FD eye was also significantly longer than the untreated eye in the FD7 group (p=0.04, FIG. 7C, relative elongation of 114±4 µm). Significant relative elongation did not occur in the FD7+LA100 animals (difference of 42±30 µm, p=0.714, FIG. 7C) showing that L-arginine treatment inhibited ocular growth. L-Arginine treatment reduced relative eye growth by 62% (reduction of 72 µm, FIG. 7D).

Figure 8:
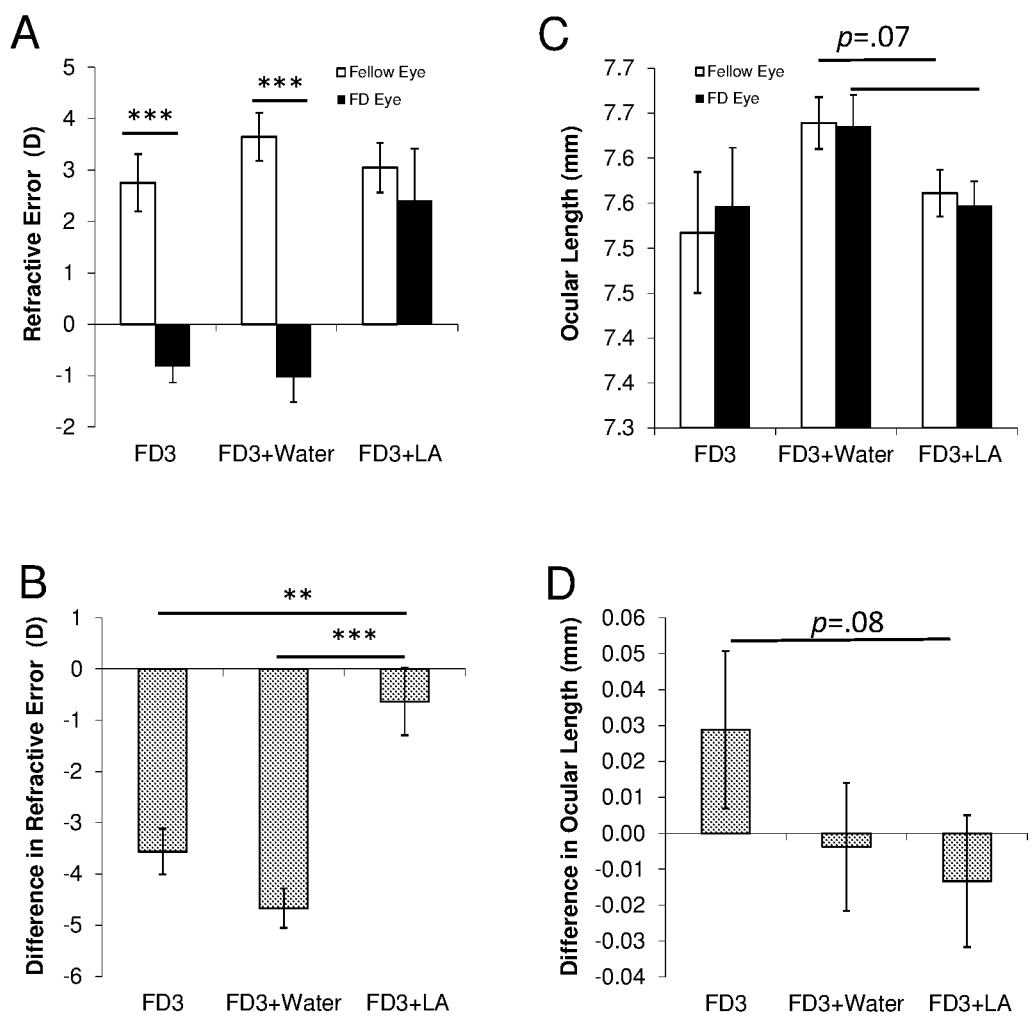
FIG. 8. Effects of twice daily feeding 25 mg/kg of L-arginine (FD3+LA) on 3 days of form deprivation (FD) in Experiment 2 (Example 4). Only one eye received FD. A. Refractive Error in each eye after 3 days of FD. B. Difference in Refractive Error between the eyes. Negative values indicate relative myopia in the FD eye. LA inhibits myopia, but water gavage does not. C. Ocular length in each eye after FD. Note the tendency for both eyes to be smaller after feeding the drug relative to feeding water. D. Difference in Ocular length between the eyes. Myopic eyes are relatively larger, while LA reduces the growth enhancing effects of FD.

Experiment 2: Effect of Twice Daily Feeding of
L-Arginine (25 mg/kg) on Myopia and Ocular
Length FD induced significantly more myopia in the FD eye compared to the fellow eye in both the FD3 and FD3+Water groups (FIG. 8A). No such relative differences were observed in the animals fed twice daily doses of 25 mg/kg of L-arginine (FIG. 8A). The average relative myopia (FD eye-fellow eye) was significantly reduced in the animals fed L-arginine compared to those fed water (reduction of +4.03D or 86%) or those not gavaged (reduction of +2.93 or 82%) (FIG. 8B).

As expected, compared to Experiment 1, 3 days of FD induced smaller changes in ocular growth (cf. FIGS. 7D and 8D). Animals fed L-arginine had smaller eye lengths than animals only fed water, and this occurred in both the FD eye and the fellow eye (FIG. 8C). The small growth enhancing effects of FD seen in animals not gavaged tended to be inhibited in animals fed water or L-arginine (FIG. 8D).

The data described above demonstrates that a single daily oral dose of L-arginine or a smaller dose of L-arginine delivered twice daily were both effective in eliminating the myopic refractive shift that accompanies form deprivation in the mammalian eye. However, both eyes (and the crystalline lens, data not shown) appear to be influenced by systemic oral doses of L-Arginine.

Example 5—Eye Drop Administration of
L-Arginine to Guinea Pigs

In this study, L-arginine was administered as eye drops to guinea pigs to determine if this simple route of administration might be effective at reducing myopia. To induce myopia without reducing light levels to the retina, the established technique of negative spectacle lens compensation was used. In a second experiment, the effects of L-arginine eye-drops on normal growth were compared with Atropine. Atropine has been tested as a treatment for myopia and is an anticholinergic drug that acts as a competitive agonist for the muscarinic acetylcholine receptor. It is used as a mydratic and cycloplegic agent to dilate the pupil and disables the ability of the eye to focus.

Methods

Guinea pigs (pigmented variety, *Cavia porcellus*) were bred, housed, and raised as described in Example 1. Lights were on a 12 hr light 12 hr dark cycle. The University of Newcastle Animal Care and ethics Committee approved all procedures.

Two experimental protocols were employed (see Table 4). In Experiment 1, young guinea pigs wore a −6D lens on one eye from 5-12 days of age. They were randomly divided within each litter into two groups of 10 animals each, and received either a drop of L-Arginine (100 mM, 1.7%) in Saline (pH 7.4) or Saline alone (0.9%, pH 7.4) twice per day in the eye wearing the lens (Table 4). Drops were administered at the beginning of their light cycle and again approximately 6 hrs later in the middle of their day cycle. Lenses were removed during the drop administration which occurred under dim red light or in darkness. A single large drop was bathed on the cornea for 3 min in the lens-wearing eye in hand held animals. A clean lens was then reintroduced onto the eye. In Experiment 2, 14 guinea pigs were given eye drops in the same manner as in Experiment 1, but in both eyes and without any lens-wear, to determine the effect of the eye drops on normal eye growth. Animals received one drop of either 1.7% L-arginine (n=7) or atropine (Minims Atropine Sulphate 1%, Bausch & Lomb, preservative free, n=7) in one eye and saline (0.9%) in the other eye twice per day from 9-16 days of age.

chamber, and the layers at the back of the eye: the retina, choroid, and sclera. Ocular length was defined as the summed measurement from the front of the cornea to the back of the sclera.

Differences between the two eyes were analysed by a 2-tailed T-tests. The mean of calculated differences between the two eyes is referred to as relative myopia or relative ocular length and the difference in the change in ocular length in the treated compared to the untreated eye as relative growth.

Results

Experiment 1: Effect of Eye Drops of L-Arginine (1.7%) on Myopia and Ocular Length At the end of lens wear period at 12 days of age, the mean refractive error in untreated eyes did not differ between the

TABLE 4

Experimental Design (RE: refractive error; USound: measurement of eye length using ultrasound).

| Experiment | Group | Drug (twice/day) | Treatment | 1st Measure | 2nd Measure | N |
|---|---|---|---|---|---|---|
| 1 | LA | 100 mM LA (1.7%) | Eye Drops twice daily and -6D lens worn on treated eye from 5-12 days of age | RE and Usound: Before First drop at 5 days of age | RE and Usound: At the start of their light cycle at 12 days of age, 12 hrs after their last drop was given | 10 |
|  | Saline | Saline 0.9% |  |  |  | 10 |
| 2 | LA | 100 mM LA (1.7%) in one one eye and Saline on the other eye | Eye Drops twice daily from 9-16 days of age | RE and Usound: At 17 days of age, 24 hrs after their last drop was given | NA | 7 |
|  | ATR | 1% Atropine in one eye and saline in the other eye |  |  |  | 7 |

In Experiment 1, at the end of the lens-wearing period, at 12 days of age just before the morning lights came on, both eyes were cyclopleged (1% Cyclopentolate—to paralyse the focussing muscles of the eye to a resting state) and 1.25 hours later, refractive error (RE) was measured. Animals were then anaesthetised with gaseous anaesthetic (1.5% isoflurane in oxygen) and eye length measures were taken in both eyes with high frequency ultrasound as described in Example 1. Biometry measures were also taken in the same manner before the lens wear period at 5 days of age. [No refractive measures were done at 5 days of age as cycloplegia could have interfered with the drug or lens response]. In Experiment 2, refractive error and eye length using ultrasound were measured in the same manner at 17 days of age, 24 hours after the previous drop was administered.

In Experiment 1, lens-induced myopia was achieved by attaching -6D concave lenses to matching Velcro arcs glued above and below the experimental eye as previously described (Howlett & McFadden, 2009). Lenses were exchanged with a clean lens after drop administration.

Figure 9:
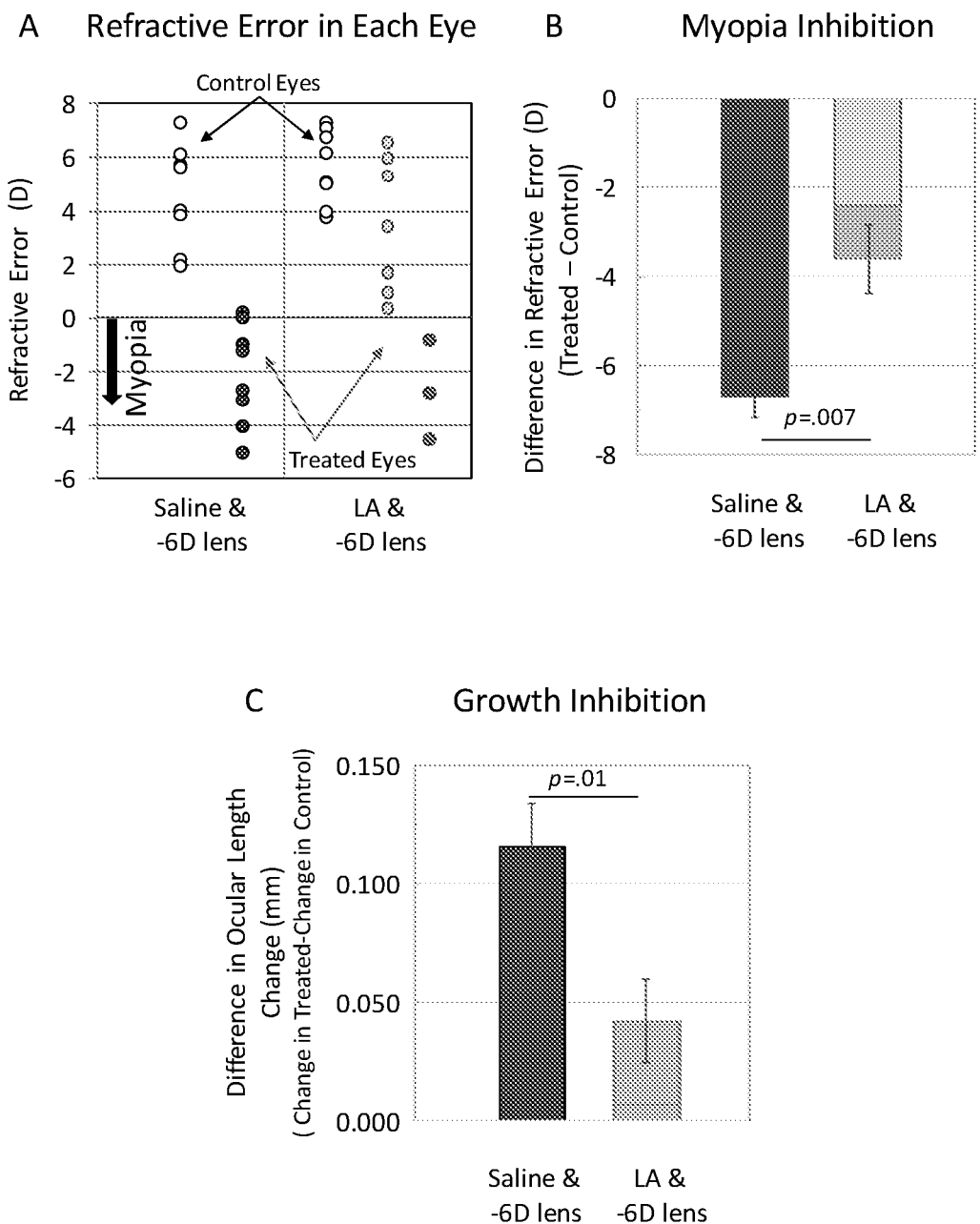
FIG. 9. The effect of eye drops administered twice daily in guinea pigs wearing a −6D lens on one eye between 9 and 12 days of age to induce myopia. A. The refractive error is shown for 10 animals given 1.7% LA and 10 animals given saline eye drops. The eye drops were given in the eye wearing a −6D lens. Data for both the lens-wearing and untreated fellow eyes is shown in each group. In the LA group, 3 animals developed myopia (i.e. less than zero), and the remaining 70% did not. In the saline group, all animals developed myopia. B. The corresponding mean relative myopia is shown for each group. C. The mean relative eye growth for both groups. In B and C, the mean for the 7 animals that did not develop myopia after LA eye drops is shown by the palest blue shading. These animals showed the same growth between the treated and untreated eyes, showing that LA eye drops completely protected the eye from myopic growth.

After cycloplegia was induced, refractive error was measured in each eye using an Autorefractor (Nidek AR-20, Japan). The spherical equivalent was calculated as the average of the sphere plus half the cylinder as is normal in clinical practice. All reported refractive errors are the spherical equivalent. Next, ocular length was measured using high frequency ultrasound (20 MHz) as previously described (McFadden et al, 2004). At least 20 traces were recorded for each eye and distances were averaged for at least 10 of these recordings. Peaks from the recordings were selected for the back of the cornea, the crystalline lens, and the vitreous two groups (LA: +5.2±0.5 D; Saline: +5.1±0.8 D, p=0.88). Significant relative myopia developed in 10/10 animals given saline eye drops sufficient to compensate for the -6D of imposed defocus (Saline: -6.7±0.5 D, p=0.000). In contrast, 7/10 animals administered LA eye drops did not develop myopia in the lens-wearing eye (FIG. 9A), and the relative myopia in these 7 animals (LA: -2.5±0.7 D, FIG. 9B light blue) or the mean across all 10 animals (LA: -3.6±0.8 D, FIG. 9B medium blue) was significantly less than that in the saline treated animals (p=0.000 and p=0.007, respectively). In summary, 1.7% LA eye drops protected the eye from developing myopia in 70% of animals, where the mean myopia was 37% of that in control animals.

The myopia induced by -6D lens wear was caused by a longer eye, making images short-focussed in front of the retina. The amount of relative eye growth between 5 and 12 days of age in control animals only given saline eye drops, was 115±18 µm; while across all animals given LA eye drops, the mean growth in ocular length was only 42±17 µm. This reduction in ocular growth caused by LA was highly significant (p=0.01, FIG. 9C), and practically no relative growth (10±12 µm, light blue, p=0.44) occurred in the 70% of animals which failed to develop myopia. This demonstrates that 1.7% LA eye drops stopped the eye from developing excessive growth, and growth was no different from normal in 70% of animals.

The data described above demonstrates that eye drops containing a 1.7% dose of L-arginine delivered twice daily were effective in reducing the myopic refractive shift that accompanies spectacle induced myopia in the mammalian eye, and importantly, completely eliminated the excessive growth normally associated with myopia.

Figure 10:
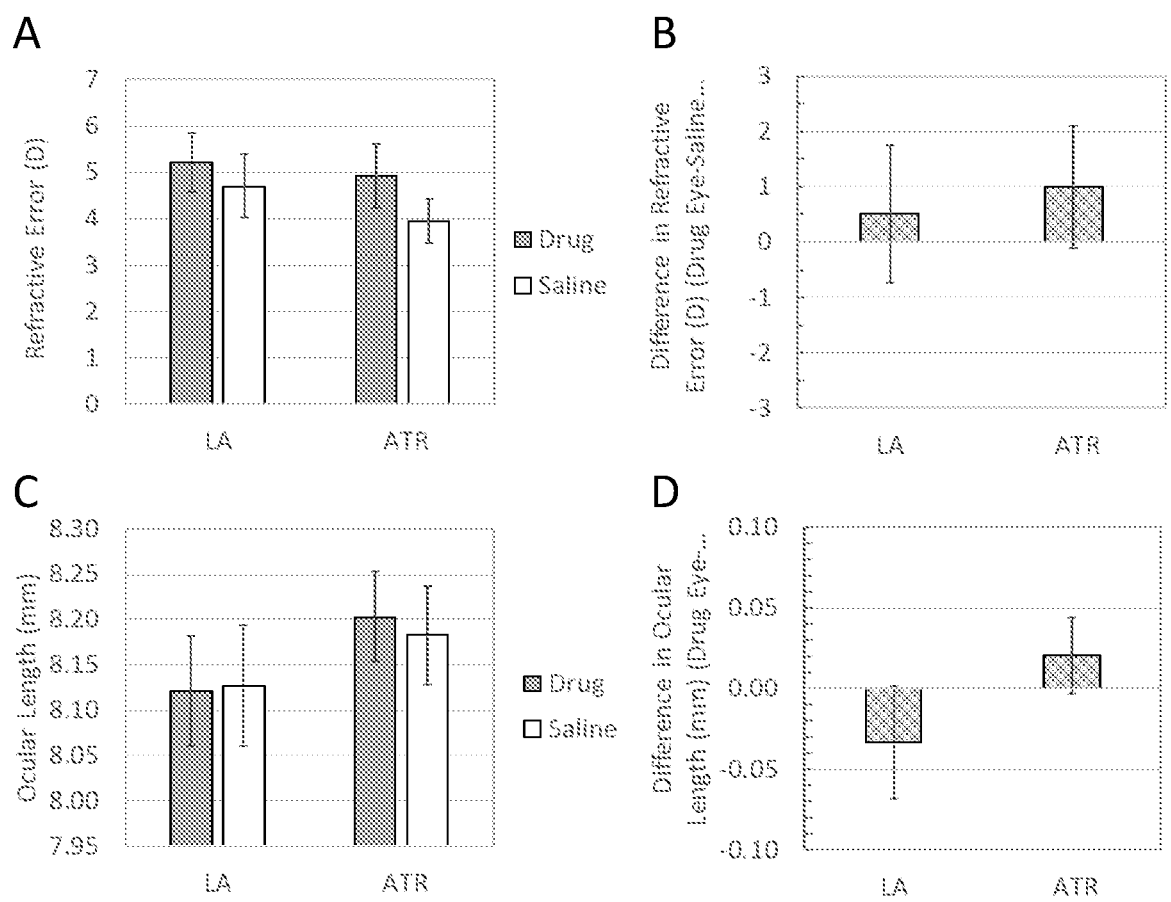
FIG. 10. The effect of eye drops administered twice daily between 9 and 16 days of age in young guinea pigs. Animals received drug eye drops in one eye and the other eye received saline eye drops (0.9%) The drugs were 1.7% L-Arginine (LA, n=7) and 1% atropine (ATR, n=7). A. The mean refractive error is shown for both eyes in each group. B. The mean difference between the two eyes in refractive error. There was a slight hyperopic shift in both cases but this was not significant. C. The corresponding mean ocular length in each eye in each drug group. D. The mean difference between the two eyes in ocular length. Neither drug significantly changed normal ocular growth. Although animals given Atropine had slightly bigger eyes on average, this difference was not significant (p=0.22).

Experiment 2: The Effects of L-Arginine Eye-Drops on Normal Growth and Emmetropization 1.7% L-arginine eye drops did not affect the refractive error of the eye (FIG. 10). There was no difference in mean refractive error between the eyes that received LA and the eyes that received saline (FIG. 10A, p=0.69). There was also no difference in mean refractive error between the two eyes in animals that received 1% topical Atropine (FIG. 10A, p=0.40). Both groups showed the same very small relative hyperopic shift in the drug treated eye (FIG. 10B), but these shifts were not significant. When both eyes were averaged, there was a tendency for the Atropine animals to have emmetropized more rapidly (in the myopic direction) than the LA animals, but this was also not significant (+5.08 and +4.43 respectively, p=0.32).

In keeping with the slightly less hyperopia in the Atropine animals, their eyes were also slightly longer on average, but not significantly so (8.124 Vs 8.192 mm, p=0.22, FIG. 10C). There was no statistical difference in ocular length in either group, with the eyes given LA drops slightly smaller than control, while the eyes given Atropine were slightly larger (LA: −33 μm, p=0.39; ATR: +20 μm, p=0.42, FIG. 10D), but this variation between the two groups was not statistically significant (p=0.22).

In summary, 1.7% LA eye drops given twice daily did not affect either normal refractive error development or ocular length, suggesting that LA can specifically target myopic growth when given in an eye drop formulation.

REFERENCES

Carpenter and Schoenfisch (2012) *Chem Soc Rev* 41:3742-3752.
Chin-Dusting et al. (2007) *Pharmacol Ther* 116:428-436.
Howlett and McFadden (2006) *Vision Res* 46:267-283.
Howlett and McFadden (2007) *Vision Res* 47:1178-1190
Howlett and McFadden (2009) *Vision Res* 49(2), 219-227
McFadden et al. (2004) *Vision Res* 44:643-653.
Miller and Megson (2007) *Br J Pharmacol* 151:305-321.

The invention claimed is:

1. A method for treating or preventing myopia, or for inhibiting the development of myopia, the method comprising administering to a subject in need thereof an effective amount of an agent that induces or promotes the expression and/or activity of neuronal nitric oxide synthase (nNOS) in one or more ocular cells thereby treating or preventing myopia or inhibiting the development of myopia.

2. The method according to claim 1, wherein the ocular cells express nNOS or are part of an nNOS producing structure in the eye.

3. The method according to claim 1, wherein the ocular cells are amacrine cells.

4. The method according to claim 1, wherein the agent that induces or promotes the expression and/or activity of nNOS in amacrine cells is L-arginine.

5. The method according to claim 1, wherein the agent is administered directly to an eye of the subject, or is administered orally or topically.

6. The method according to claim 5, wherein the administration is via intravitreal, conjunctival or scleral injection or an intravitreal, conjunctival or scleral implant.

7. The method according to claim 1, wherein the myopia is lens- or instrument-induced myopia, simple myopia, early or late-onset myopia, progressive myopia, degenerative myopia or pathological myopia.

8. The method according to claim 1, wherein the treatment, prevention or inhibition of development of myopia comprises inhibiting or preventing the progression of myopia in a myopic eye, reversing established myopia, or inhibiting or preventing the development of myopia in an eye predisposed thereto or at risk of developing myopia.

* * * * *